United States Patent
Haick et al.

(10) Patent No.: US 9,315,848 B2
(45) Date of Patent: Apr. 19, 2016

(54) VOLATILE ORGANIC COMPOUNDS FOR DETECTING CELL DYSPLASIA AND GENETIC ALTERATIONS ASSOCIATED WITH LUNG CANCER

(75) Inventors: Hossam Haick, Haifa (IL); Nir Peled, Hod Hasharon (IL)

(73) Assignees: TECHNION RESEARCH AND DEVELOPMENT FOUNDATION LTD., Haifa (IL); THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 328 days.

(21) Appl. No.: 13/817,285

(22) PCT Filed: Aug. 17, 2011

(86) PCT No.: PCT/IL2011/000667
§ 371 (c)(1),
(2), (4) Date: Feb. 15, 2013

(87) PCT Pub. No.: WO2012/023138
PCT Pub. Date: Feb. 23, 2012

(65) Prior Publication Data
US 2013/0143247 A1 Jun. 6, 2013

Related U.S. Application Data

(60) Provisional application No. 61/374,635, filed on Aug. 18, 2010.

(51) Int. Cl.
| *C12Q 1/02* | (2006.01) |
| *C12Q 1/48* | (2006.01) |
| *G01N 30/00* | (2006.01) |
| *H01J 49/00* | (2006.01) |
| *C12Q 1/68* | (2006.01) |
| *G01N 33/574* | (2006.01) |
| *G01N 30/88* | (2006.01) |

(52) U.S. Cl.
CPC ............... *C12Q 1/025* (2013.01); *C12Q 1/485* (2013.01); *C12Q 1/6886* (2013.01); *G01N 30/00* (2013.01); *G01N 33/57423* (2013.01); *H01J 49/0027* (2013.01); *C12Q 2600/156* (2013.01); *G01N 2030/8854* (2013.01); *G01N 2333/71* (2013.01); *G01N 2333/82* (2013.01); *Y10T 436/212* (2015.01); *Y10T 436/214* (2015.01); *Y10T 436/216* (2015.01); *Y10T 436/24* (2015.01)

(58) Field of Classification Search
CPC .................. Y10T 436/200833; Y10T 436/21; Y10T 436/212; Y10T 436/214; Y10T 436/216; Y10T 436/24; C12Q 1/02; C12Q 1/025; C12Q 1/485; C12Q 1/6886; C12Q 2600/156; G01N 33/48; G01N 33/574; G01N 33/57423; G01N 30/00; G01N 2030/8854; G01N 2333/71; G01N 2333/82; G01N 2800/52; G01N 2800/60; H01J 49/0027

USPC .............. 436/63, 64, 86, 128, 139–142, 161, 436/173; 435/4, 15, 29; 422/83, 84, 89, 98; 250/281, 282; 73/23.35

See application file for complete search history.

(56) References Cited

U.S. PATENT DOCUMENTS

| 4,772,559 | A | 9/1988 | Preti |
| 5,693,715 | A | 12/1997 | Kodali |
| 5,996,586 | A | 12/1999 | Phillips |
| 6,540,691 | B1 | 4/2003 | Phillips |
| 2008/0220984 | A1 | 9/2008 | Bright |
| 2010/0099658 | A1 | 4/2010 | Kondoh |
| 2010/0137733 | A1 | 6/2010 | Wang |
| 2010/0173285 | A1 | 7/2010 | Varmus |

FOREIGN PATENT DOCUMENTS

| EP | 1416278 A1 | 5/2004 |
| EP | 1447043 A1 | 8/2004 |
| WO | 00/41623 A1 | 7/2000 |
| WO | 01/42504 A2 | 6/2001 |
| WO | 03/014724 A1 | 2/2003 |
| WO | 2004/008953 A1 | 1/2004 |
| WO | 2006/112733 A1 | 10/2006 |
| WO | 2008/151238 A1 | 12/2008 |
| WO | 2009/004576 A1 | 1/2009 |
| WO | 2009/066293 A1 | 5/2009 |
| WO | 2009/118205 A2 | 10/2009 |
| WO | 2009/144725 A1 | 12/2009 |
| WO | 2010/079490 A1 | 7/2010 |
| WO | 2010/079491 A1 | 7/2010 |
| WO | 2011/083473 A1 | 7/2011 |

OTHER PUBLICATIONS

Peled et al. Nanomedicine: Nanotechnology, Biology, and Medicine, vol. 9, 2013, pp. 758-766.*
Silkoff et al., "ATS/ERS Recommendations for Standardized Procedures for the Online and Offline Measurement of Exhaled Lower Respiratory Nitric Oxide and Nasal Nitric Oxide". Am J Respir Crit Care Med 171: 912-930, (2005).
Soda et al., "Identification of the transforming EML4-ALK fusion gene in non-small-cell lung cancer". Nature 448(7153): 561-566, (2007).
Soda et al., "A mouse model for EML4-Alk-positive lung cancer". PNAS USA 105(50): 19893-19897, (2008).
Solomon et al., "ALK gene rearrangements: a new therapeutic target in a molecularly defined subset of non-small cell lung cancer". J Thorac Oncol 4(12): 1450-1454, (2009).

(Continued)

*Primary Examiner* — Maureen Wallenhorst
(74) *Attorney, Agent, or Firm* — Browdy and Neimark, PLLC

(57) ABSTRACT

The present invention provides methods of identifying a genetic abnormality such as mutation in EGFR or KRAS or ALK which is associated with the management of lung cancer or diagnosing, prognosing or monitoring the treatment of pre-cancerous conditions of the lung, such as bronchial dysplasia or atypical alveolar hyperplasia (AAH), through the detection of at least one volatile organic compound indicative of these states.

20 Claims, 23 Drawing Sheets

(56) References Cited

OTHER PUBLICATIONS

Song et al., "Quantitative breath analysis of volatile organic compounds of lung cancer patients". Lung Cancer 67(2): 227-231, (2010).
Sponring et al., "Release of volatile organic compounds from the lung cancer cell line NCI-H2087 in vitro". Anticancer Res 29(1) 419-426, (2009).
Wehinger et al., "Lung cancer detection by proton transfer reaction mass-spectrometric analysis of human breath gas". Inter J Mass Spectrometry 265(1): 49-59, (2007).
Witschi et al., "Metabolism and pulmonary toxicity of butylated hydroxytoluene (BHT)". Pharmacol Ther 42(1): 89-113, (1989).
Wong et al., "The EML4-ALK fusion gene is involved in various histologic types of lung cancers from nonsmokers with wild-type EGFR and KRAS". Cancer 115(8): 1723-1733, (2009).
Yu et al., "Detection volatile organic compounds in breath as markers of lung cancer using a novel electronic nose". Sensors. Proceedings of IEEE 2 1333-1337, (2003).
Zimmermann et al., "Determination of volatile products of human colon cell line metabolism by GC/MS analysis". Metabolomics 3(1): 13-17, (2007).
Roger Gomm "Social Research Methodology" Palgreave macmillan. 2 : 80-83 (2008).
Zhengjie, He, et al. "Gas Chromatography-Mass Spectrometric Analysis for Volatile Organic Compound of Human Metabolites in Sealed Cabin." Chinese Journal of Analytical Chemistry 29.8 : 978-982. (2001).
Xu "The Role of Maintenance Therapy and Biomarkers in Frontline Therapy for Advanced Non-Small-Cell Lung Cancer". A Summary of Selected Presentations From the 45th Annual Meeting of the American Society of Clinical Oncology, Orlando, FL (May 29-Jun. 2, 2009).
Barash et al., "Sniffing the unique "odor print" of non-small-cell lung cancer with gold nanoparticles", Small 5(22): 2618-2624, (2009).
Buszewski et al., "Human exhaled air analytics: biomarkers of diseases", Biomed Chromatogr 2(6): 553-566, (2007).
Chan et al., "Elevated levels of oxidative stress markers in exhaled breath condensate", Journal of Thoracic Oncology 4(2): 172-178, (2009).
Chen et al., "A study of an electronic nose for detection of lung cancer based on a virtual SAW gas sensors array and imaging recognition method", Meas Sci Technol 16(8): 1535-1546, (2005).
Chen et al., "A study of the volatile organic compounds exhaled by lung cancer cells in vitro for breath diagnosis", Cancer 110(4): 835-844, (2007).
Chiarle et al., "The anaplastic lymphoma kinase in the pathogenesis of cancer". Nat Rev Cancer 8(1): 11-23, (2008).
Coate et al., "Molecular predictive and prognostic markers in non-small-cell lung cancer". Lancet Oncol 10(10): 1001-1010, (2009).
Coelho et al., "Breath air analysis and its use as a biomarker in biological monitoring of occupational and environmental exposure to chemical agents". J Chromatography B 853(1-2): 1-9, (2007).
Coggiola et al., "Volatile organic biomarkers in exhaled breath as a rapid prodromal, diagnosis of bioagent infection". SRI International, Menlo Park CA, 2004.
Di Natale et al., "Lung cancer identification by the analysis of breath by means of an array of non-selective gas sensors". Biosens Bioelectron 18(10): 1209-1218, (2003).
Dovgolevsky et al., "Direct observation of the transition point between quasi-spherical and cubic nanoparticles in a two-step seed-mediated growth method". Small 4(11): 2059-2066, (2008).
Dovgolevsky et al., "Chemically sensitive resistors based on monolayer-capped cubic nanoparticles: towards configurable nanoporous sensors". Small 5(10): 1158-1161, (2009).
Dovgolevsky et al., "Monolayer-Capped Cubic Platinum Nanoparticles for Sensing Nonpolar Analytes in Highly Humid Atmospheres". J Phys Chem C 114(33): 14042-14049, (2010).

Filipiak et al., "Release of volatile organic compounds (VOCs) from the lung cancer cell line CALU-1 in vitro". Cancer Cell Int 8: 17, (2008).
Gaspar et al., "Organic metabolites in exhaled human breath—a multivariate approach for identification of biomarkers in lung disorders". J Chromatogr A 1216(14): 2749-2756, (2009).
Gautschi et al., "Circulating deoxyribonucleic acid as prognostic marker in non-small cell lung cancer patients undergoing chemotherapy". J Clin Oncol 22(20): 4157-4164, (2004).
Gautschi et al., "Origin and prognostic value of circulating KRAS mutations in lung cancer patients". Cancer Lett 254 (2): 265-273, (2007).
Gordon et al., "Volatile organic compounds in exhaled air from patients with lung cancer". Clin Chem 31(8): 1278-1282, (1985).
Herth et al., "Narrow-band imaging bronchoscopy increases the specificity of bronchoscopic early lung cancer detection". J Thorac Oncol 4(9): 1060-1065, (2009).
Ionescu et al., "Quantitative analysis of NO2 in the presence of CO using a single tungsten oxide semiconductor sensor and dynamic signal processing". Analyst 127(9): 1237-1246, (2002).
Jemal et al., "Cancer statistics". CA Cancer J Clin 59(4): 225-249, (2009).
Lacroix et al., "Gene expression profiling of non-small-cell lung cancer". Expert Rev Mol Diagn 8(2): 167-178, (2008).
Lindinger et al., "On-line monitoring of volatile organic compounds at pptv levels by means of proton-transfer-reaction mass spectrometry (PTR-MS) medical applications, food control and environmental research". Int J Mass Spectrom Ion Process 173(3): 191-241, (1998).
Lindinger et al., "Environmental, food and medical applications of proton-transfer-reaction mass spectrometry (PTR-MS)". Adv Gas Phase Ion Chem 4: 1-35, (2001).
Lynch et al., "Activating mutations in the epidermal growth factor receptor underlying responsiveness of non-small-cell lung cancer to gefitinib". N Engl J Med 350(21): 2129-2139, (2004).
Mack et al., "EGFR Mutations Detected in Plasma Are Associated with Patient Outcomes in Erlotinib Plus Docetaxel-Treated Non-small Cell Lung Cancer". J Thorac Oncol 4(12): 1466-1472, (2009).
Maheswaran et al., "Detection of mutations in EGFR in circulating lung-cancer cells". N Engl J Med 359(4): 366-377, (2008).
Mano., "Non-solid oncogenes in solid tumors: EML4-ALK fusion genes in lung cancer". Cancer Sci 99(12): 2349-2355, (2008).
Matsumura et al., "Urinary volatile compound as biomarkers for lung cancer: A proof of principle study using odor signatures in mouse models of lung cancer". PLos One 5(1): 1-11, (2009).
Miekisch et al., "Diagnostic potential of breath analysis—focus on volatile organic compounds". Clin Chim Acta 347 (1-2): 25-39, (2004).
Mok et al., "Gefitinib or carboplatin-paclitaxel in pulmonary adenocarcinoma". N Engl J Med 361(10): 947-957, (2009).
O'neill et al., "A Computerized Classification Technique for Screening for the Presence of Breath Biomarkers in Lung Cancer". Clin Chem 34(8): 1613-1617, (1988).
Ouyang and Pawliszyn., "SPME in environmental analysis". Anal Bioanal Chem 386(4): 1059-1073, (2006).
Paez et al., "EGFR mutations in lung cancer: correlation with clinical response to gefitinib therapy". Science 304(5676): 1497-1500, (2004).
Peled et al., "Predictive and prognostic markers for epidermal growth factor receptor inhibitor therapy in non-small cell lung cancer". Ther Adv Med Oncol 1(3): 137-144, (2009).
Peng et al., "Detecting simulated patterns of lung cancer biomarkers by random network of single-walled carbon nanotubes coated with nonpolymeric organic materials". Nano Lett 8(11): 3631-3635, (2008).
Peng et al., "Diagnosing lung cancer in exhaled breath using gold nanoparticles". Nature Nanotechnol 4(10): 669-673, (2009).
Peng et al., "Detection of lung, breast, colorectal, and prostate cancers from exhaled breath using a single array of nanosensors". Br J Cancer 103(4): 542-551, (2010).
Phillips et al., "Volatile organic compounds in breath as markers of lung cancer: a cross-sectional study". Lancet 353 (9168): 1930-1933, (1999).

(56) References Cited

OTHER PUBLICATIONS

Phillips et al., "Detection of lung cancer with volatile markers in the breath". Chest 123(6): 2115-2123, (2003).

Phillips et al., "Volatile markers of breast cancer in the breath". Breast J 9(3): 184-191, (2003).

Phillips et al., "Prediction of breast cancer using volatile biomarkers in the breath". Breast Cancer Res Treat 99(1): 19-21, (2006).

Phillips et al., "Prediction of lung cancer using volatile biomarkers in breath". Cancer Biomark 3(2): 95-109, (2007).

Phillips et al., "Detection of lung cancer using weighted digital analysis of breath biomarkers". Clin Chim Acta 393(2): 76-84, (2008).

Poli et al., "Exhaled volatile organic compounds in patients with non-small cell lung cancer: cross sectional and nested short-term follow-up study". Respir Res 6: 71-81, (2005).

Poli et al., "Breath analysis in non small cell lung cancer patients after surgical tumour resection". Acta Biomed 79(1): 64-72, (2008).

Riely et al., "Clinical course of patients with non-small cell lung cancer and epidermal growth factor receptor exon 19 and exon 21 mutations treated with gefitinib or erlotinib". Clin Cancer Res 12(3 Pt 1): 839-844, (2006).

Rock et al., "Electronic nose: current status and future trends". Chem Rev 108(2): 705-725, (2008).

Schmutzhard et al., "Pilot study: volatile organic compounds as a diagnostic marker for head and neck tumors". Head Neck 30(6): 743-749, (2008).

Shaw et al., "Clinical features and outcome of patients with non-small-cell lung cancer who harbor EML4-ALK". J Clin Oncol 27(26): 4247-4253, (2009).

Barash et al., (2012) Classification of lung cancer histology by gold nanoparticle sensors. Nanomedicine 8(5): 580-9.

Hakim et al., (2012) Volatile Organic Compounds of Lung Cancer and Possible Biochemical Pathways. Chem Rev 112 (11): 5949-5966.

Peled et al., (2012) Detection of volatile organic compounds in cattle naturally infected with Mycobacterium bovis. Sensors and Actuators B: Chemical 171-172: 588-594.

Peled et al., (2012) Non-invasive breath analysis of pulmonary nodules. J Thorac Oncol 7(10): 1528-33.

Phillips et al., (1999) Variation in volatile organic compounds in the breath of normal humans. J Chromatogr B Biomed Sci Appl 729(1-2): 75-88.

* cited by examiner

VOLATILE ORGANIC COMPOUNDS FOR DETECTING CELL DYSPLASIA AND GENETIC ALTERATIONS ASSOCIATED WITH LUNG CANCER

FIELD OF THE INVENTION

The present invention relates to methods of diagnosing, prognosing or monitoring the treatment of pre-cancerous conditions of the lung e.g. bronchial dysplasia or atypical alveolar hyperplasia (AAH), or identifying a genetic alteration which is associated with lung cancer as a means of prognosing or monitoring the treatment or the recurrence of lung cancer, or predicting a patient's response and/or resistance to various treatment regimens.

BACKGROUND OF THE INVENTION

Novel approaches for prediction and early diagnosis of lung cancer are based on mutation analysis and the detection of atypical changes in the cell structure (Lacroix et al., Expert Review Mol Diagn (2008) 8(2) 167-178). The main mutations which are associated with lung cancer are Epidermal Growth Factor Receptor (EGFR) mutations and V-Ki-ras2 Kirsten ras sarcoma viral oncogene homolog (KRAS) mutations. The EGFR is a 170-kD transmembrane protein which is a member of the receptor kinase family. EGFR is widely expressed in several malignancies including lung, breast, colon, esophageal and others. Activating mutations in exons 18-21 of EGFR were initially identified in non-small cell lung carcinoma (NSCLC) patients with clinical response to gefitinib (Lynch et al., N Engl J Med (2004) 350(21) 2129-2139; Paez et al., Science (2004) 304(5676) 1497-1500). Patients with EGFR mutations have a greater response rate to EGFR-targeted therapy than patients with wild type EGFR or unknown mutation status (10-20%) (Riely et al., Clin Cancer Res (2006) 12(3 Pt 1) 839-844). Recent studies suggest that EGFR-targeted therapy is preferred over chemotherapy in chemo-naïve patients with EGFR mutations. Mok et al. (N Engl J Med 2009 361) showed that the presence of an EGFR mutation was found to be a robust predictor of improved progression-free survival with gefitinib, as compared with carboplatin-paclitaxel. Peled et al. (Ther Adv Med Oncol (2009) 1(3) 137-144) discloses that there are several biomarkers including EGFR mutation status, EGFR protein expression, EGFR gene copy number, and a serum proteomin marker that are able to direct and predict the result of EGFR-related therapies in NSCLC.

Additional mutations that have been suggested for the direction of anti-cancer therapy in lung cancer are KRAS mutations. KRAS is an important downstream mediator of EGFR signaling and harbors an activating mutation in codon 12 or 13 (exon 2) in approximately 10-30% of NSCLC cases. EGFR and KRAS activating mutations are almost always mutually exclusive. In NSCLC, KRAS mutation has been demonstrated to be associated with poor prognosis and is thus a negative prognostic factor, which needs to be taken into account when the predictive performance/response is assessed.

The echinoderm microtubule-associated protein like-4/anaplastic lymphoma kinase (EML4-ALK) translocation results from a small inversion within chromosome 2p and has been associated with approximately 5% to 13% of lung cancers (Chiarle et al., Nat Rev Cancer (2008) 8 11-23; Mano, Cancer Sci (2008) 99 2349-2355; Shaw et al., J Clin Oncol (2009) 27 4247-4253; and Wong et al., Cancer (2009) 115 1723-1733). The resulting EML4/ALK fusion protein possesses potent oncogenic activity through the Ras/Raf, PI3K/Akt, and JAK/STAT pathways, which are also stimulated by EGFR (Soda et al., PNAS USA (2008) 105 19893-19897; and Solomon et al., J Thorac Oncol (2009) 4 1450-1454). In transgenic mice expressing the EML4-ALK fusion protein in lung alveolar epithelial cells, hundreds of tumors develop within a few weeks of birth. The tumors can be effectively inhibited by small molecules that target ALK, supporting a role for EML4-ALK as a promoter of lung tumorigenesis (Soda et al., PNAS USA (2008) 105 19893-19897). Epidemiologically, patients with tumors expressing the EML4-ALK fusion tend to be younger males, have a never/light smoking history and have tumors with adenocarcinoma histology, specifically the signet ring subtype (Shaw et al., J Clin Oncol (2009) 27 4247-4253). Patients whose tumors express the EML4-ALK fusion often do not respond to EGFR tyrosine kinase inhibitors (Shaw et al., J Clin Oncol (2009) 27 4247-4253). Activity of an EML4-ALK inhibitor was observed in a phase I trial in patients with NSCLC whose tumors were EML4-ALK-positive. Other agents that target the ALK pathway are currently in development (Solomon et al., J Thorac Oncol (2009) 4 1450-1454).

In order to determine the existence of a mutation/genetic abnormality in a cancer cell, DNA gene sequencing along with Polymerase Chain Reaction (PCR) amplification is required. Other methods include gene array analysis that is based on RNA sequencing, and immunohistochemistry techniques in which antibodies to a specific protein are used. However, such procedures are expensive, time consuming, require specialists in analyzing the results and are not suitable for non-resectable tumors. Another evolving technique is circulating DNA which can be detected in the plasma and serum of patients (Gautschi et al., J Clin Oncol (2005) 23(36) 9105). The levels of circulating DNA are associated with a poor Tumor-specific DNA alterations (such as loss of heterozygosity), promoter methylation, and KRAS and EGFR mutations. New techniques for capturing circulating tumor cells enable the detection of EGFR-activating mutations, and the drug-resistance allele T790M. Such techniques appear to be more sensitive than those for capturing circulating DNA. Furthermore, a decline in the number of circulating tumor cells was associated with tumor response to radiography (Maheswaran et al., Engl J Med (2008) 359 (4) 366). However, all available conventional methods for the detection and identification of cancer genetic mutations lack the requisite sensitivity to enable clinical utility (Mack et al., J. Thorac. Oncol. (2009) 4(2) 1466). In addition, they are significantly affected by the presence of stromal (and/or connective) tissue in the specimen taken. More importantly, cancer cells change their characteristics over time; new mutations occur frequently in the metastasic lesions and/or in the primary area over time. These mutations require frequent monitoring using invasive procedures.

Dysplasia or dysplastic changes are atypical changes in the nuclei of cells, the cytoplasm, or the growth pattern of cells. These changes which vary from subtle changes to pronounced changes are considered pre-cancerous conditions. Dysplasia is characterized by four major pathological microscopic changes as follows: anisocytosis (cells of unequal size), poikilocytosis (abnormally shaped cells), hyperchromatism (degeneration of cell nuclei, which become filled with particles of pigment (chromatin)), and the presence of mitotic figures (an unusual number of cells which are currently dividing). As the risk for cancer increases with the progression of the dysplasia, detecting dysplasia allows focusing on the high-risk cohort and defining the group for specific follow up and/or treatment, e.g. routine bronchoscopies, chemoprevention therapy, etc.

Atypical alveolar hyperplasia (AAH) has recently been described in human lungs in association with primary lung cancer, particularly adenocarcinoma. Unlike proximal bronchogenic carcinoma, peripheral (parenchymal) adenocarcinoma of the lung does not have a well-recognized progenitor lesion. Epidemiological morphometric, and cytofluorometric data in the literature suggest that AAH is a candidate premalignant entity.

Several investigative tools have been proposed for the detection of pre-invasive lesions and early lung cancers. Spiral CT scanning is not suitable for detecting such findings in the central airways, especially the early stages of pre-invasive squamous cell carcinoma, which account for 17-29% of all lung cancers (Jemal et al., CA Cancer J Clin (2009) 59(4), 225-249). White light bronchoscopy (WBL) is also considered insufficient for detecting such lesions. Auto fluorescence bronchoscopy (AFB) uses a helium-cadmium laser to illuminate the bronchial mucosa with 442-nm light. The red and green autofluorescence emitted light is captured by photoamplifier camera and is presented as green for normal areas and red brown for abnormal areas. During the last few years, a new bronchoscope, the Narrow-band Imaging Bronchoscope (NBI), has been evaluated to detect bronchial dysplasia and carcinoma in situ. The NBI uses two bandwidths of light: 390-445 nm (blue) light that is absorbed by superficial capillaries and 530-550 nm (green) light that is absorbed by blood vessels below the mucosal capillaries. These narrow bandwidths reduce the scattering of light and enable enhanced visualization of blood vessels (Herth et al., J Thorac Oncol (2009) 4(9) 1060-1065) thus increasing the sensitivity in detecting bronchial dysplasia and metaplasia. EP 1447043 discloses an apparatus for imaging diagnosis of tissue using diagnostic white light endoscopy (DWLE) and diagnostic auto fluorescence endoscopy (DAFE).

Several predictive and prognostic markers have been suggested for the identification of dysplastic conditions and early diagnosis of lung cancer (Coate et al., Lancet Oncol (2009) 10 1001-1010). Specific genetic abnormalities that increase the risk for cancer as well as those which occur in cancerous tissue (and not in normal tissue) were found to be significant for the therapy through specific pathway that might be associated with the carcinogenesis of the tumor. For example, Soda et al. (Nature (2007) 448 561-567) discloses that a small inversion within chromosome 2p results in the formation of a fusion gene comprising portions of the echinoderm microtubule-associated protein-like 4 (EML4) gene and the anaplastic lymphoma kinase (ALK) gene in NSCLC cells. WO 2009/118205 discloses means for the diagnosis, prognosis and/or treatment monitoring of lung cancer or bronchial dysplasia, and the use thereof for predicting and monitoring therapeutic intervention in dysplasia or cancer patients using at least one peptide. WO 2001/042504 discloses the detection of specific extracellular nucleic acid derived from mutant oncogenes or other tumor-associated DNA in plasma or serum fractions of human or animal blood associated with neoplastic, pre-malignant or proliferative disease. EP 1416278 discloses a method for improved diagnosis of dysplasias based on simultaneous detection of INK4a gene products and at least one marker for cell proliferation.

Volatile Organic Compounds

Volatile organic compounds (VOCs) are small organic molecules released during cellular metabolic processes. Patterns of VOCs are known to be used as biomarkers of various diseases. In exhaled breath of patients with cancer, elevated levels of certain VOCs including volatile $C_4$-$C_{20}$ alkane compounds, specific monomethylated alkanes as well as benzene derivatives were found.

In recent years many attempts have been made to identify one specific pattern of volatile organic compounds (VOCs) in the breath of lung cancer patients. Phillips et al. (Lancet (1999) 353 1930-1933) used discriminant analysis to detect a combination of 22 breath VOCs as the "fingerprint" of lung cancer. Phillips et al. (Chest (2003) 123 2115-2123) then used a predictive model employing 9 VOCs which was found to exhibit sufficient sensitivity and specificity to be used as screen for lung cancer. In a more recent study, Phillips et al. (Cancer Biomarkers (2007) 3 95-109) described the use of multi-linear regression and fuzzy logic to analyze breath samples of lung cancer patients. This study provided a set of 16 VOCs as the major identifiers of primary lung cancer in breath. The use of weighted digital analysis to select 30 breath VOCs as candidate biomarkers of primary lung cancer was then employed (Phillips et al., Clinica Chimica Acta (2008) 393 76-84).

Yu et al. (Sensors, Proceedings of IEEE (2003) 2 1333-1337) used an electronic nose device with capillary column GC and a pair of surface acoustic wave sensors to detect 9 VOCs as markers for lung cancer. Chen et al. (Meas Sci Technol (2005) 16 1535-1546) used a set of 11 VOCs to calibrate sensors array based on surface acoustic wave to diagnose lung cancer patients. In another study, Chen et al. (Cancer (2007) 110 835-844) identified 4 special VOCs that were found to exist in all culture mediums of lung cancer cells and can be used as markers of lung cancer. Di Natale et al. (Biosensors and Bioelectronics (2003) 18 1209-1218) used an array of non-selective gas sensors for detecting various alkanes and benzene derivatives as possible candidate markers of lung cancer. Gordon et al. (Clin Chem (1985) 31(8) 1278-1282) used breath collection technique and computer-assisted gas chromatography/mass spectrometry to identify several volatile organic compounds in the exhaled breath of lung cancer patients which appear to be associated with the disease. Song et al. (Lung Cancer (2009) 67 227-231) reported that 1-butanol and 3-hydroxy-2-butanone were found at significantly higher concentrations in the breath of the lung cancer patients compared to the controls. These two VOCs are thus potential biomarkers useful for diagnosing lung cancer. O'neill et al. (Clinical Chemistry (1988) 34(8) 1613-1617) reported a list of 28 VOCs found in over 90% occurrence in expired-air samples from lung cancer patients. Wehinger et al. (Inter J Mass Spectrometry (2007) 265 49-59) used proton transfer reaction mass-spectrometric analysis to detect lung cancer in human breath. Two VOCs were found to best discriminate between exhaled breath of primary lung cancer cases and control. Gaspar et al. (J Chromatography A (2009) 1216 2749-2756) used linear and branched $C_{14}$-$C_{24}$ hydrocarbons from exhaled air of lung cancer patients, smokers and non-smokers for multivariable analysis to identify biomarkers in lung disorders. Poli et al. (Respiratory Research (2005) 6 71-81) showed that the combination of 13 VOCs allowed the correct classification of cases into groups of smokers, patients with chronic obstructive pulmonary disease, patients with non-small cells lung cancer and controls. Recently, Poli et al. (Acta Biomed (2008) 79(1) 64-72) measured VOC levels in exhaled breath of operated lung cancer patients, one months and three years after surgical removal of the tumor. Peng et al. (Nature Nanotech (2009) 4 669-673) identified 42 VOCs that represent lung cancer biomarkers using gas chromatography/mass spectrometry.

In addition to the many studies that were aimed at identifying VOCs indicative of lung cancer from breath samples, Filipiak et al. (Cancer Cell International (2008) 8 17) disclosed a list of 60 substances observed in the headspace of medium as well as in the headspace of lung cancer cell line CALU-1. Barash et al. (Small (2009) 5(22) 2618-2624) discloses a list of 15 VOCs which were found in the headspace of non-small cell lung carcinoma samples. These VOCs were not found in the headspace of control cell lines. Sponring et al. (Anticancer Res (2009) 29(1) 419) found that at least two substances, 2-methylpentane and 2-ethyl-1-hexanol, can be released from the NCI-H2087 lung cancer cell line. These studies cumulatively provided over 150 VOCs as potential lung cancer biomarkers in breath samples.

WO 2000/041623 discloses a process for determining the presence or absence of a disease, particularly breast or lung cancer, in a mammal, comprising collecting a representative sample of alveolar breath and a representative sample of ambient air, analyzing the samples of breath and air to determine content of n-alkanes having 2 to 20 carbon atoms, inclusive, calculating the alveolar gradients of the n-alkanes in the breath sample in order to determine the alkane profile, and comparing the alkane profile to baseline alkane profiles calculated for mammals known to be free of the disease to be determined, wherein finding of differences in the alkane profile from the baseline alkane profile being indicative of the presence of the disease.

WO 2010/079491 to one of the inventors of the present invention discloses a set of volatile organic compounds indicative of lung cancer, and methods of diagnosing or monitoring lung cancer progression using such set of volatile organic compounds.

There is an unmet need for the identification of genetic abnormalities such as EGFR and KRAS mutations and/or ALK-ELM translocation and for the identification of atypical changes in lung/bronchial cells for the prediction, early diagnosis and targeted treatment of lung cancer.

SUMMARY OF THE INVENTION

The present invention provides the detection of genetic abnormalities, such as a mutation in EGFR or KRAS, or an ALK-ELM4 translocation or CMET amplification which have significant implication in lung cancer through the detection of at least one volatile organic compound biomarker. The detection of genetic abnormalities further provides the prediction of the response or resistance (primary and/or acquired) to specific therapy which is based on modulators of the activity of EGFR tyrosine kinase and/or anaplastic lymphoma kinase or other downstream signaling associated with the above (e.g. IGF1R activation). The present invention further provides the diagnosis and monitoring of pre-cancerous conditions of the lung which is associated with increased risk of developing lung cancer through the detection of at least one volatile organic compound.

The invention is based in part on the unexpected finding that the presence of a signature set of volatile organic compounds can be used as a biomarker for dysplasia, particularly bronchial dysplasia, or atypical alveolar hyperplasia (AAH). Additionally, disclosed herein for the first time is the use of at least one volatile organic compound from the breath of a subject or the headspace of a container in which cancerous or pre-cancerous tissue of the subject has been deposited, for identifying a genetic alteration selected from an EGFR/KRAS mutation, ALK-ELM4 translocation and CMET amplification. The identification of these genetic alterations provides the prediction and monitoring of the response to a treatment regimen based on, e.g., modulators of EGFR or ALK. The present invention thus provides methods of diagnosis, mutation analysis, monitoring of treatment, prognosis assessment and prediction of responses or resistance to anti-cancer therapy (classical chemotherapy and/or targeted therapy).

According to one aspect, the present invention provides a method of identifying a genetic alteration selected from a mutation in EGFR, a mutation in KRAS, an ALK-ELM4 translocation and c-MET amplification, wherein the genetic alteration is associated with lung cancer, the method comprising the steps of: a) obtaining a sample from a test subject; b) determining the level of at least one volatile organic compound in the test sample; and c) comparing the level of the at least one volatile organic compound from the test sample with the level of said at least one volatile organic compound in a negative control sample, whereby a significantly different level of said at least one volatile organic compound in the test sample as compared to the level of said compound in the negative control sample is indicative of the presence of said genetic alteration.

In one embodiment, the EGFR mutation is a T790M mutation.

In some embodiments, the at least one volatile organic compound indicative of the genetic alteration is selected from the group consisting of 4-methyl-1-heptanol, acetic acid octyl ester, decane, 3-methyl-decane, octanal, pentadecanenitrile, and tetradecene. Each possibility represents a separate embodiment of the invention. In other embodiments, the at least one volatile organic compound indicative of the genetic alteration is selected from the group consisting of 4-methyl-1-heptanol, 6-methyl-1-heptanol, 2-ethyl-1-hexanol, acetic acid octyl ester, benzaldehyde, decance, 3-methyl-dodecance, tetrahydrofuran, isopropyl myristate, octanal, pentadecanenitrile, 2,2,4-trimethyl-pentanenitrile, 2,2,4-trimethyl-3-carboxyisopropyl-isobutyl ester pentanoic acid, phenol, styrene, tetradecance, 4-methyl-tetradecane, toluene, tridecane, 6-methyl-tridecane, and undecance. Each possibility represents a separate embodiment of the invention. In further embodiments, the at least one volatile organic compound indicative of the genetic alteration is selected from the group consisting of triethylamine, 2-hydroxy benzaldehyde, and decanal. Each possibility represents a separate embodiment of the present invention. In additional embodiments, the at least one volatile organic compound indicative of the genetic alteration is selected from the group consisting of triethylamine, toluene, styrene, benzaldehyde, 2-hydroxy benzaldehyde, decanal, phenol and 2-ethyl-1-hexanol. Each possibility represents a separate embodiment of the present invention.

In another embodiment, the method provides the prognosis of lung cancer. In a further embodiment, the method provides the differentiation between healthy subjects and subjects having a genetic alteration associated with lung cancer. In other embodiments, the method further provides the differentiation between healthy subjects, subjects having an EGFR mutation, subjects having a KRAS mutation, subjects having an ALK-ELM4 translocation and subjects having CMET amplification. Each possibility represents a separate embodiment of the invention.

In certain embodiments, the present invention provides a method of identifying a mutation in EGFR (e.g. a T790M mutation) comprising determining the level of at least one volatile organic compound selected from triethylamine, toluene, styrene, decanal, phenol and 2-ethyl-1-hexanol in the test sample and comparing said level with the level of said at least one volatile organic compound in a control sample, whereby a significantly different level of said at least one volatile organic compound in the test sample as compared to the level of said compound in the control sample is indicative of the presence of said mutation in EGFR.

In other embodiments, the present invention provides a method of identifying an ALK-ELM4 translocation comprising determining the level of at least one volatile organic compound selected from triethylamine, toluene, 2-hydroxy benzaldehyde and decanal in the test sample and comparing said level with the level of said at least one volatile organic compound in a control sample, whereby a significantly different level of said at least one volatile organic compound in the test sample as compared to the level of said compound in the control sample is indicative of the presence of said ALK-ELM4 translocation.

In certain embodiments, the present invention provides a method of identifying a mutation in KRAS comprising determining the level of at least one volatile organic compound selected from benzaldehyde and 2-hydroxy benzaldehyde in the test sample and comparing said level with the level of said at least one volatile organic compound in a control sample, whereby a significantly different level of said at least one volatile organic compound in the test sample as compared to the level of said compound in the control sample is indicative of the presence of said mutation in KRAS.

In some embodiments, the method is directed to prognosing or monitoring the treatment of lung cancer, or predicting a patient's response to a treatment regimen.

According to another aspect, the present invention provides a method of predicting the response or resistance to a tyrosine kinase modulator or monitoring treatment with said tyrosine kinase modulator by identifying a genetic alteration associated with lung cancer, the genetic alteration selected from a mutation in EGFR, a mutation in KRAS, an ALK-ELM4 translocation and CMET amplification, the method comprising the steps of: (a) obtaining a sample from a test subject; (b) determining the level of at least one volatile organic compound in the test sample, wherein the volatile organic compound is selected from 4-methyl-1-heptanol, acetic acid octyl ester, decane, 3-methyl-decane, octanal, pentadecanenitrile, and tetradecene; and (c) comparing the level of the at least one volatile organic compound from the test sample with the level of said at least one volatile organic compound in a control sample, whereby a significantly different level of said at least one volatile organic compound in the test sample as compared to the level of said compound in the control sample is indicative of said genetic alteration and therefore provides the prediction and assessment of response or resistance to said treatment.

In various embodiments, the tyrosine kinase modulator is selected from the group consisting of Axitinib, Bosutinib, Cediranib, Crizotinib, Dasatinib, Erlotinib, Gefitinib, Imatinib, Lapatinib, Lestaurtinib, Nilotinib, Semaxanib, Sunitinib, and Vandetanib. Each possibility represents a separate embodiment of the invention.

In certain embodiments, the at least one volatile organic compound for prognosing, monitoring or predicting the response to the treatment of lung cancer by identifying a genetic alteration associated with lung cancer is selected from the group consisting of 4-methyl-1-heptanol, 6-methyl-1-heptanol, 2-ethyl-1-hexanol, acetic acid octyl ester, benzaldehyde, decance, 3-methyl-dodecance, tetrahydrofuran, isopropyl myristate, octanal, pentadecanenitrile, 2,2,4-trimethyl-pentanenitrile, 2,2,4-trimethyl-3-carboxyisopropyl-isobutyl ester pentanoic acid, phenol, styrene, tetradecance, 4-methyl-tetradecane, toluene, tridecane, 6-methyl-tridecane, and undecance. Each possibility represents a separate embodiment of the invention. In further embodiments, the at least one volatile organic compound for prognosing, monitoring or predicting the response to the treatment of lung cancer by identifying a genetic alteration associated with lung cancer is selected from the group consisting of triethylamine, 2-hydroxy benzaldehyde, and decanal. Each possibility represents a separate embodiment of the present invention. In additional embodiments, the at least one volatile organic compound for prognosing, monitoring or predicting the response to the treatment of lung cancer by identifying a genetic alteration associated with lung cancer is selected from the group consisting of triethylamine, toluene, styrene, benzaldehyde, 2-hydroxy benzaldehyde, decanal, phenol and 2-ethyl-1-hexanol. Each possibility represents a separate embodiment of the present invention.

According to yet another aspect, the present invention provides a method of diagnosing, prognosing or monitoring the treatment of pre-cancerous conditions of the lung or bronchial dysplasia or atypical alveolar hyperplasia (AAH), the method comprising the steps of: a) obtaining a sample from a test subject; b) determining the level of at least one volatile organic compound from a set of volatile organic compounds in the test sample, wherein the set of volatile organic compounds comprises at least one of 6-ethyl-undecane, 2,6-dimethyl-octane, 2,6-dimethyl-heptadecane, 3-(bromomethyl)-heptane, and 4,6-dimethyl-dodecane; and c) comparing the level of the at least one volatile organic compound from the test sample with the level of said at least one volatile organic compound in a control sample, whereby a significantly different level of said at least one volatile organic compound in the test sample as compared to the level of said compound in the control sample is indicative of the presence of pre-cancerous conditions of the lung or bronchial dysplasia or atypical alveolar hyperplasia (AAH). Each possibility represents a separate embodiment of the present invention.

In particular embodiments, the set of volatile organic compounds indicative of pre-cancerous conditions of the lung or bronchial dysplasia or AAH comprises at least one additional volatile organic compound selected from the group consisting of 5-(2-methylpropyl)-nonane, and 3-methyl-nonane. Each possibility represents a separate embodiment of the invention.

In other embodiments, the set of volatile organic compounds indicative of pre-cancerous conditions of the lung or bronchial dysplasia or AAH further comprises at least one additional volatile organic compound selected from the group consisting of 2-heptanone, undecane, heptadecane, 2,4-hexadiene, 2,2,3-trimethyl-cyclohexane, 3,7-dimethyl-2-octene, 3,3,5-trimethyl-cyclohexanone, 1-chloro-decane, borneol, 1,2,3,4-tetrahydro-naphthalene, and 4,9,9-trifluoro-bicyclo [6.1.0]nona-2,4,6-triene. Each possibility represents a separate embodiment of the invention.

In certain embodiments, the method of diagnosing, prognosing or monitoring the treatment of pre-cancerous conditions of the lung or bronchial dysplasia or AAH further provides the differentiation between healthy subjects, subjects having lung cancer, subjects having bronchial dysplasia, subjects having AAH, subjects with different stages of lung cancer and subjects with different stages of bronchial dysplasia. Each possibility represents a separate embodiment of the invention.

In various embodiments, the step of determining the level of at least one volatile organic compound in the test sample comprises the use of at least one technique selected from the group consisting of an olfactory system, gas-chromatography (CC), GC-lined mass-spectrometry (GC-MS), a proton transfer reaction mass-spectrometry (PTR-MS), and quartz crystal microbalance (QCM). Each possibility represents a separate embodiment of the invention. In one currently preferred embodiment, the step of determining the level of at least one volatile organic compound in the test sample comprises the use of an olfactory system through measuring a change in any one or more of an electrical property of the system such as, but not limited to, conductivity, resistance, impedance, capacitance, inductance, or optical properties upon exposure to the VOC to be detected. Each possibility represents a separate embodiment of the invention.

In an alternative embodiment, the step of determining the level of the at least one volatile organic compound in a test sample comprises the use of Gas-Chromatography-Mass Spectrometry (GC-MS) combined with solid phase microextraction (SPME).

In specific embodiments, solid phase microextraction comprises the use of extraction fibers coated with at least one of polydimethylsiloxane, divinylbenzene, carboxen and combinations thereof. Each possibility represents a separate embodiment of the invention.

In particular embodiments, solid phase microextraction comprises the use of extraction fibers coated with at least one polymer selected from the group consisting of polydimethylsiloxane, polydimethylsiloxane-divinylbenzene and polydimethylsiloxane-carboxen. Each possibility represents a separate embodiment of the invention.

In certain embodiments, the level of the at least one volatile organic compound in the test sample is significantly increased as compared to the level of said compound in a control sample. According to other embodiments, the level of the at least one volatile organic compound in the test sample is significantly decreased as compared to the level of said compound in a control sample.

In particular embodiments, the levels of a plurality of volatile organic compounds in the test sample form a pattern which is significantly different from the pattern of said volatile organic compounds in a control sample. According to further embodiments, the pattern is significantly different from a predetermined pattern of occurrence of volatile organic compounds in control samples.

The pattern can be analyzed with a pattern recognition analyzer which utilizes various algorithms including, but not limited to, artificial neural networks, multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART) and statistical methods including, but not limited to, principal component analysis (PCA), partial least squares (PLS), multiple linear regression (MLR), principal component regression (PCR), discriminant function analysis (DFA) including linear discriminant analysis (LDA), and cluster analysis including nearest neighbor. Each possibility represents a separate embodiment of the invention.

In an exemplary embodiment, the algorithm used to analyze the pattern is principal component analysis (PCA). In another exemplary embodiment, the algorithm used to analyze the pattern is discriminant function analysis (DFA). In other embodiments, the pattern can be analyzed using support vector machine (SVM) analysis.

According to various embodiments, the control sample may be obtained from a reference group comprising subjects which are not afflicted with lung cancer or bronchial dysplasia or atypical alveolar hyperplasia (AAH) (negative control). In alternative embodiments, the control sample may be obtained from a population of patients known to be afflicted with lung cancer or bronchial dysplasia or AAH or which have a genetic alteration according to the principles of the present invention (positive control). The control sample, according to the principles of the present invention is obtained from at least one subject, preferably a plurality of subjects. A set of control samples from subjects who are not afflicted with lung cancer or bronchial dysplasia or AAH or which do not have an EGFR mutation, a KRAS mutation, ALK-ELM4 translocation or CMET amplification may be stored as a reference collection of data.

In certain embodiments, the test subject is a mammal, preferably a human.

In particular embodiments, the present invention provides the monitoring of the treatment of pre-cancerous conditions of the lung with a chemoprevention agent, preferably illioprost or a cox-2 inhibitor.

In other embodiments, the test sample or specimen is selected from the group consisting of a breath sample, a tissue sample, a serum sample, a urine sample, feces, a sweat sample, a vaginal discharge, a saliva sample and sperm. Each possibility represents a separate embodiment of the invention. In particular embodiments, the sample is obtained from the headspace of a container in which at least one bodily specimen has been deposited. In specific embodiments, the methods of the present invention are applicable for detecting at least one VOC from a container comprising a tissue sample. In some embodiments, the tissue sample comprises a histological section. In particular embodiments, the tissue sample comprises cells.

In yet other embodiments, the methods of the present invention are applicable for detecting at least one VOC in an exhaled breath sample. In exemplary embodiments, the methods of the present invention further comprise the step of increasing VOC concentration using an apparatus for collecting breath samples. In specific embodiments, the apparatus is designed to collect alveolar breath. In other embodiments, the apparatus comprises at least one of a breath concentrator and a dehumidifying unit.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 9A: GC-MS analysis of immortal bronchial cells (▲), SCLC (pentagons), and NSCLC (●); FIG. 9B: GC-MS analysis of immortal bronchial cells (▲) and sub-categories of NSCLC (adenocarcinoma (▫) and squamous cell carcinoma (●)).

FIGS. 15A-15C represent the three comprehensive tests that contain all 37 headspace samples. FIGS. 15D-15I represent six additional tests to better characterize the samples in cases of misclassifications in one or more of the constituent tests. The standard distribution (SD) of the CV1 values is represented by the error bars. The boxes represent the 95% confidence intervals of the CV1 values, corresponding to 1.96*standard deviation (SE).

FIGS. 17A-17C. Sensing features selected by SVM analysis from the organically functionalized gold nanoparticles' multidimensional data output for optimal separation between headspace samples from: FIG. 17A: Lung cancer (LC; ●) and immortal bronchial epithelium cells (IBE; ▲), FIG. 17B: NSCLC (●) and SCLC (◇) cells; and FIG. 17C: sub-categories of NSCLC, namely adeno-(✺) and squamous-(●) cell carcinoma cells.

DETAILED DESCRIPTION OF THE INVENTION

Figure 1:
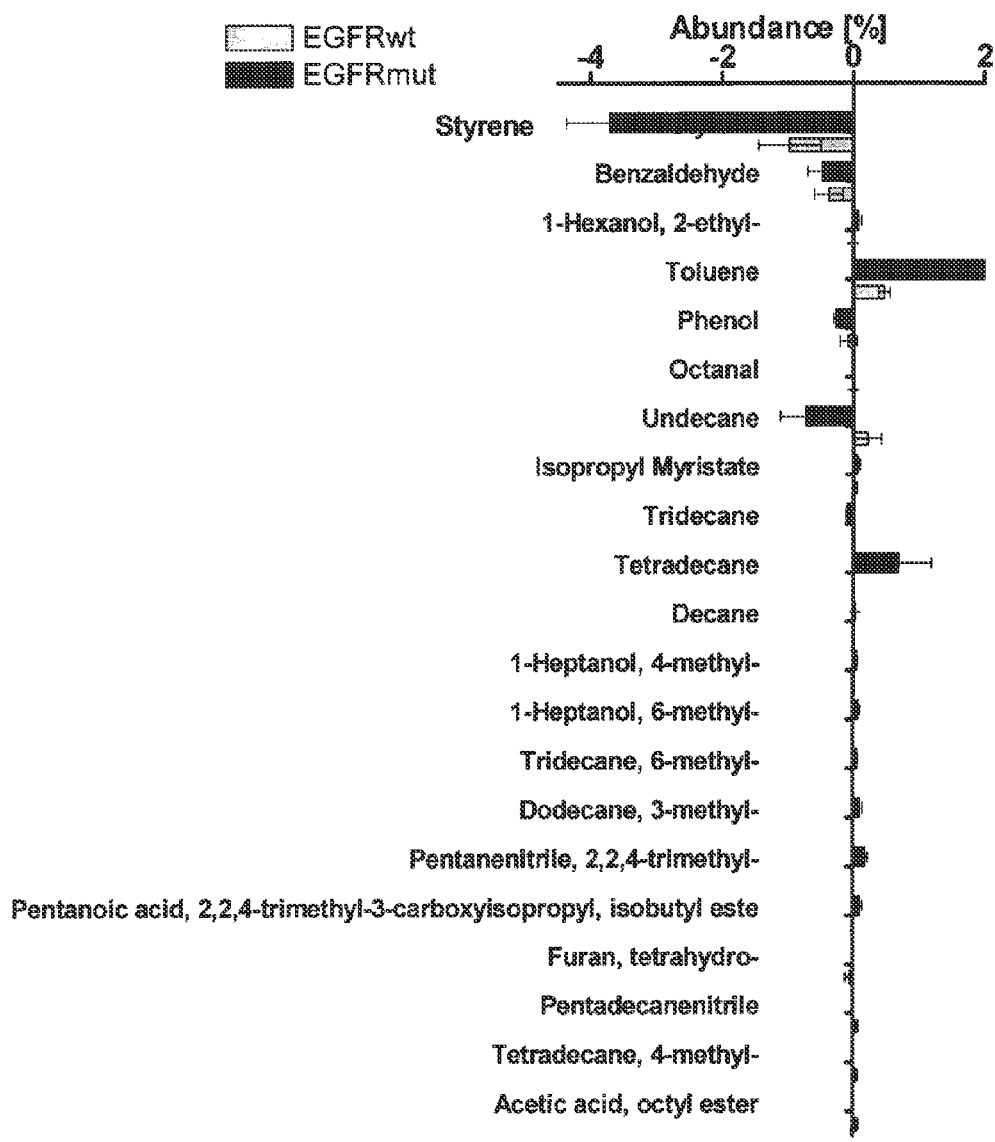
FIG. 1. GC-MS analysis of cells having an EGFR mutation (EGFRmut) and cells having wild type EGFR (EGFRwt).

The present invention provides methods of diagnosing, prognosing or monitoring the treatment of bronchial dysplasia or AAH, or identifying a genetic alteration which is associated with lung cancer and with its treatment/prognosis, the method comprising the detection of at least one volatile organic compound indicative of these states.

Further, the present invention provides a unique set of volatile organic compounds as biomarkers for bronchial dysplasia or AAH, which define a tendency or high risk to develop lung cancer. The present invention provides the prediction of the onset of lung cancer and further provides the monitoring of targeted treatment of lung cancer at its earlier stages thus resulting in an increase in the rate of success of such treatment.

The present invention provides a method of identifying a genetic alteration which is associated with lung cancer, and use of such identification for prognosis, prediction of treatment, and treatment monitoring of a subject having lung cancer. The method involves the following steps: once a test sample is provided, the level of at least one VOC which is indicative of the alteration is determined. The level of the at least one VOC in the test sample is then compared to a control sample whereby a significantly different level in the test sample is indicative of the alteration. The term "genetic alteration which is associated with lung cancer" as used herein refers to a chromosomal abnormality such as, but not limited to, a change in chromosome number (aneuploidy), a change in a gene copy number (amplification, deletion, duplication, aneuploidy), potential breakpoint, insertion, inversion, rearrangement, or translocation. Specifically, this term includes, but is not limited to, EGFR or KRAS mutations, ALK-ELM4 translocation, CMET amplification and the like. EGFR mutations include, but are not limited to, activating mutations in exons 18-21 of EGFR, deletions in exon 19, substitution mutations in exon 21 (e.g. L858R), mutations in exon 20 (T790M mutations) or less common mutations (e.g., G719X, L861Q). KRAS mutations include, but are not limited to, activating mutation in exon 2 at codon 12 or 13.

Thus, in some embodiments the present invention provides a method of identifying a genetic alteration selected from a mutation in EGFR, a mutation in KRAS, an ALK-ELM4 translocation and c-MET amplification, wherein the genetic alteration is associated with lung cancer. The method comprises a) determining the level of at least one volatile organic compound in a test sample; and b) comparing the level of the at least one volatile organic compound from the test sample with the level of said at least one volatile organic compound in a negative control sample, whereby a significantly different level of said at least one volatile organic compound in the test sample as compared to the level of said compound in the negative control sample is indicative of the presence of said genetic alteration.

The identification of a genetic alteration associated with lung cancer further provides the differentiation between test samples obtained from healthy subjects (subjects who do not have at least one of said genetic alterations) and test samples obtained from subjects having at least one of said genetic alterations associated with lung cancer. In additional embodiments, the identification of a genetic alteration associated with lung cancer further provides the differentiation between samples obtained from different subgroups of subjects having a genetic alteration associated with lung cancer including, but not limited to, subjects having an EGFR mutation, subjects having a KRAS mutation, subjects having an ALK-ELM4 translocation and subjects having a c-MET amplification.

According to the principles of the present invention, the method further provide the prediction of the treatment and allows for monitoring of the treatment of lung cancer which is associated with the genetic alteration, wherein the treatment comprises the use of a tyrosine kinase modulator, preferably a tyrosine kinase inhibitor. In accordance with these embodiments, the present invention provides a method of predicting the response or resistance to a tyrosine kinase modulator or monitoring treatment with said tyrosine kinase modulator by identifying a genetic alteration associated with lung cancer, the genetic alteration selected from a mutation in EGFR, a mutation in KRAS, an ALK-ELM4 translocation and CMET amplification. The method comprises a) determining the level of at least one volatile organic compound in a test sample, wherein the volatile organic compound is selected from 4-methyl-1-heptanol, acetic acid octyl ester, decane, 3-methyl-decane, octanal, pentadecanenitrile, and tetradecene; and b) comparing the level of the at least one volatile organic compound from the test sample with the level of said at least one volatile organic compound in a control sample, whereby a significantly different level of said at least one volatile organic compound in the test sample as compared to the level of said compound in the control sample is indicative of said genetic alteration and therefore provides the prediction and assessment of response or resistance to said treatment.

Further volatile organic compounds which are indicative of these genetic alterations include, but are not limited to, 4-methyl-1-heptanol, 6-methyl-1-heptanol, 2-ethyl-1-hexanol, acetic acid octyl ester, benzaldehyde, decance, 3-methyl-dodecance, tetrahydrofuran, isopropyl myristate, octanal, pentadecanenitrile, 2,2,4-trimethyl-pentanenitrile, 2,2,4-trimethyl-3-carboxyisopropyl-isobutyl ester pentanoic acid, phenol, styrene, tetradecane, 4-methyl-tetradecane, toluene, tridecane, 6-methyl-tridecane, and undecance. Each possibility represents a separate embodiment of the invention. Additional volatile organic compounds as biomarkers for these genetic alterations include, but are not limited to, triethylamine, 2-hydroxy benzaldehyde, and decanal. Each possibility represents a separate embodiment of the present invention. In some embodiments, the volatile organic compounds which can be used as biomarkers for the genetic alterations disclosed herein include, but are not limited to, triethylamine, toluene, styrene, benzaldehyde, 2-hydroxy benzaldehyde, decanal, phenol and 2-ethyl-1-hexanol. Each possibility represents a separate embodiment of the present invention.

Tyrosine kinase inhibitors within the scope of the present invention include, but are not limited to, Axitinib, Bosutinib, Cediranib, Crizotinib, Dasatinib, Erlotinib, Gefitinib, Imatinib, Lapatinib, Lestaurtinib, Nilotinib, Semaxanib, Sunitinib, and Vandetanib. Each possibility represents a separate embodiment of the invention.

The present invention further provides a set of volatile organic compounds which are indicative of dysplasia or AAH, the set comprising at least one volatile organic compound selected from 6-ethyl-undecane, 2,6-dimethyl octane, 2,6-dimethyl-heptadecane, 3-bromomethyl-heptane and 4,6-dimethyl-dodecane. Each possibility represents a separate embodiment of the invention. This set provides the diagnosis, prognosis or monitoring the treatment of bronchial dysplasia or AAH or early stages of lung cancer. Thus, the present invention provides a method of diagnosing, prognosing or monitoring the treatment of pre-cancerous conditions of the lung or bronchial dysplasia or AAH. The method comprises a) determining the level of at least one volatile organic compound from the set of volatile organic compounds which are indicative of dysplasia or AAH in a test sample; and b) comparing the level of the at least one volatile organic compound from the test sample with the level of said at least one volatile organic compound in a control sample, whereby a significantly different level of said at least one volatile organic compound in the test sample as compared to the level of said compound in the control sample is indicative of pre-cancerous conditions of the lung or bronchial dysplasia or AAH. The set of VOCs may further include at least one of 5-2-methylpropyl nonane and 3-methyl nonane. Each possibility represents a separate embodiment of the invention. Additional VOCs which may be further included in the set as biomarkers for dysplasia or AAH are selected from 2-heptanone, undecane, heptadecane, 2,4-hexadiene, 2,2,3-trimethyl-cyclohexane, 3,7-dimethyl-2-octene, 3,3,5-trimethyl-cyclohexanone, 1-chloro-decane, borneol, 1,2,3,4-tetrahydro-naphthalene, and 4,9,9-trifluoro-bicyclo[6.1.0]nona-2,4,6-triene. Each possibility represents a separate embodiment of the invention.

In some embodiments, the method of diagnosing, prognosing or monitoring the treatment of pre-cancerous conditions of the lung or bronchial dysplasia or AAH provides the differentiation between test samples obtained from healthy subjects (subjects who do not have pre-cancerous conditions of the lung or bronchial dysplasia or AAH), test samples obtained from subjects having bronchial dysplasia, test samples obtained from subjects having AAH, and test samples obtained from subjects having lung cancer. Each possibility represents a separate embodiment of the invention. In additional embodiments, the present invention provides the differentiation between test samples obtained from subjects having different stages of lung cancer and between test samples obtained from subjects having different stages of bronchial dysplasia. Each possibility represents a separate embodiment of the invention.

The present invention further provides the monitoring of the treatment of dysplasia with an agent selected from illioprost and cox-2 inhibitors. Each possibility represents a separate embodiment of the invention. The terms "dysplasia" or "dysplastic changes" as use herein refer to pre-cancerous conditions characterized by atypical changes in the nuclei of cells (particularly changes in the DNA), the cytoplasm (the portion of the cell surrounding the nuclei), or in the growth pattern of cells. The terms refers to low grade dysplasia which is characterized by some atypical changes which occur in some of the cells but not in all cells and by a normal growth pattern of the glands, and to high-grade dysplasia (also called "carcinoma in-situ") which is the most advanced dysplasia with atypical changes in many of the cells and a very abnormal growth pattern of the glands.

The present invention further provides a method of diagnosing lung cancer from a tissue sample, the method comprising the steps of: a) obtaining a tissue sample comprising lung cells from a test subject; b) determining the level of at least one volatile organic compound released from the tissue sample; and c) comparing the level of the at least one volatile organic compound released from the tissue sample with the level of said at least one volatile organic compound in a control sample, whereby a significantly different level of said at least one volatile organic compound released from the tissue sample as compared to the level of said compound in the control sample is indicative of the presence of lung cancer. In one embodiment, the volatile organic compounds are indicative of genetic alterations as described herein.

In some embodiments, the method of diagnosing lung cancer from a tissue sample further provides the differentiation between healthy tissue, a tissue comprising small-cell lung cancer cells, a tissue comprising non-small-cell lung cancer cells, and a tissue comprising immortal bronchial cells. Each possibility represents a separate embodiment of the invention. In further embodiments, the method of diagnosing lung cancer from a tissue sample further provides the differentiation between a tissue comprising non-small-cell lung cancer cells selected from a tissue comprising adenocarcinoma cells and a tissue comprising squamous cell carcinoma cells.

The volatile organic compounds which can be used to diagnose lung cancer from a tissue sample include, but are not limited to, phenol, isopropyl myristate, 2-undecanone, decanal, 1-dodecene, undecanal, nonanal, hexadecane, tridecane, tetradecane, N,N-dibutyl-formamide, 3-methyl-undecane, 1,3-bis(1,1-dimethyl)benzene, acetophenone, 2-methyl dodecane, 2,5-cyclohexadiene-1-4-d, 3-methyl trodecane, 2-ethyl-1-hexanol, 4-methyl tetradecane, 2-methyl-hexadecane, 7-methyl-tridecane, 5-methyl-2-(1-methylethyl)-acetate-1-hexanol, 2,5-dimethyl dodecane, 5-methyl-1-heptanol, 2,2,4-trimethyl-pentanenitrile, acetic acid octyl ester, 4-methyl-1-heptanol, N-butyl benzenesulfonamide, pentyl cyclopentane, 5-methyl-1heptanol, and 2,4,dimethyl-undecance. Each possibility represents a separate embodiment of the invention. Additional VOCs which can be used to diagnose lung cancer from a tissue sample include, but are not limited to, styrene, benzaldehyde, toluene, octanal, decane, 1-dodecene, 3-methyl-tridecane, triethylamine, α,α-dim benzenemethanol, hexadecanenitrile, and 5,9-undecadien-2-one. Each possibility represents a separate embodiment of the invention. In particular, the VOCs which are indicative of lung cancer and can be used to diagnose lung cancer from a tissue sample include, but are not limited to, benzaldehyde, nonanal, decanal, tetradecane, 5-methyl-tridecane, 6-methyl-5-heptene-2-one, acetophenone, 2,4-bis(1,1-dimethylethyl)-phenol, 2-ethyl-1-hexanol, 1,3-bis(1,1-dimethylethyl)-benzene, 1,3-dimethyl-benzene, and styrene. Each possibility represents a separate embodiment of the present invention.

The methods of the present invention utilize at least one technique including, but not limited to, an olfactory system (electronic nose device), Gas-Chromatography (GC), GC-lined Mass-Spectrometry (GC-MS), Proton Transfer Reaction Mass-Spectrometry (PTR-MS), and Quartz Crystal Microbalance (QCM). Each possibility represents a separate embodiment of the invention.

Olfactory systems perform odor detection through the use of an array of broadly cross-reactive sensors in conjunction with pattern recognition methods (Rock et al., Chem Rev (2008) 108 705-725). In contrast to the "lock-and-key" approach, each sensor in the system is broadly responsive to a variety of odorants. In this architecture, each analyte produces a distinct fingerprint from the array of broadly cross-reactive sensors. This allows to considerably widen the variety of compounds to which a given matrix is sensitive, to increase the degree of component identification and, in specific cases, to perform an analysis of individual components in complex multi-component (bio) chemical media. Pattern recognition algorithms can then be used to obtain information on the identity, properties and concentration of the vapor exposed to the olfactory system. Exemplary olfactory systems within the scope of the present invention include, but are not limited to, systems disclosed in e.g. WO 2009/066293 and WO 2010/079490, the contents of each of these references are hereby incorporated in their entirety. Sensing upon exposure to a VOC may be induced through a change in any one or more of conductivity, resistance, impedance, capacitance, inductance, or optical properties. Each possibility represents a separate embodiment of the invention. For electronically induced sensing, electrical contacts can be induced by methods well known in the art. When optically induced sensing is employed, sensing is performed through measuring a change in polarization upon reflection of polarized light from a surface. Measurement of the electronically or optically induced signals is performed by a detection means as is known in the art.

Gas Chromatography (GC) linked to mass spectrometry (ms) is often used to determine the chemical identity and composition of breath VOCs (Miekisch et al., Clinica Chimica Acta (2004) 347 25-39). In this set-up, the GC utilizes a capillary column having characteristic dimensions (length, diameter, film thickness) as well as characteristic phase properties. The difference in the chemical properties of different molecules in a mixture allows the separation of the molecules as the sample travels through the column, wherein each molecule has a characteristic time (termed retention time) in which it passes through the column under set conditions. This allows the mass spectrometer to capture, ionize, accelerate, deflect, and detect the ionized molecules separately. The MS signal is obtained by ionization of the molecules or molecular fragments and measurement of their mass to charge ratio by comparing it to a reference collection. The GCMS may further be combined with a Solid Phase Microextraction (SPME). The SPME technique is based on a fiber coated with a liquid (polymer), a solid (sorbent), or combination thereof. The fiber coating extracts the compounds from the sample either by absorption (where the coating is liquid) or by adsorption (where the coating is solid). The SPME fiber is then inserted directly into the sensing device for desorption and subsequent analysis (Ouyang et al., Anal Bioanal Chem (2006) 386 1059; Coelho et al, J Chromatography B (2007) 853 1). Non-limiting examples of coating include divinylbenzene, carboxen, polydimethylsiloxane, polydimethylsiloxane-divinylbenzene and polydimethylsiloxane-carboxen. Each possibility represents a separate embodiment of the invention.

Proton transfer reaction-mass spectrometry (PTR-MS) is reviewed in Lindinger et al. (Int J Mass Spectrom Ion Process (1998) 173 191-241) and Lindinger et al. (Adv Gas Phase Ion Chem (2001) 4 191-241). Briefly, PTR-MS measures VOCs which react with $H_3O^+$ ions that are added from an ion source. VOCs with a proton affinity that is larger than that of water (166.5 kcal×mol$^{-1}$) undergo a proton-transfer reaction with the $H_3O^+$ ions as follows: $H_3O^+ + R \rightarrow RH^+ + H_2O$. At the end of the drift tube reactor, a fraction of the ions is sampled by a quadrupole mass spectrometer, which measures the $H_3O^+$ and $RH^+$ ions. The ion signal at a certain mass is linearly dependent on the concentration of the precursor VOC in the sample air. In PTR-MS only the mass of VOCs is determined, causing some ambiguity in the identity of the VOCs. Thus, this technique does not allow a separate detection of different VOCs having the same mass. Further overlap of ion masses is caused by a limited degree of ion fragmentation and ion clustering in the drift tube.

Quartz Crystal Microbalance (QCM) is a piezoelectric-based device which can measure very small mass changes, mostly down to few nanograms. Briefly, QCM works by sending an electrical signal through a gold-plated quartz crystal, which causes vibrations in the crystal at a specific resonant frequency measured by the QCM. The resulted frequency shift can be translated to a change in mass on the QCM surface, mostly via using the Sauerbrey equation:

$$\Delta f = \frac{-2f_0^2}{A\sqrt{\rho_q \mu_q}} \Delta m$$

This equitation is used to correlate changes in the oscillation frequency of a piezoelectric crystal ($\Delta f$) with the mass deposited on it ($\Delta m$). Other parameters which affect the signals are the resonant frequency ($f_0$), the area between electrodes of the piezo-electric crystal (A), density ($\rho_q$) and shear modulus ($\mu_q$) of quartz.

The method of the present invention comprises a comparison between the level of at least one VOC in a test sample and the level of the VOC in a control sample whereby a significantly different level in the test sample as compared to the control sample is indicative of dysplasia or AAH or the existence of a genetic alteration according to the principles of the present invention.

The term "significantly different" as used herein refers to a statistically significant quantitative difference between the levels. A statistically significant difference can be determined by any test known to the person skilled in the art. Common tests for statistical significance include, among others, t-test, ANOVA1 Kruskal-Wallis, Wilcoxon, Mann-Whitney and odds ration. Individual samples (of unknown status) can be compared with data from the reference group (negative control), and/or compared with data obtained from a positive control group known to have lung cancer/dysplasia/EGFR mutation/KRAS mutation/ALK-ELM4 translocation/c-MET amplification. A set of control samples (positive and negative) can be stored as a reference collection for multiple analyses. An increase or decrease in the level as compared to a control or reference value or mean control level or reference value, or a change, difference or deviation from a control or reference value, can be considered to exist if the level differs from the control level or reference value, by about 5% or more, by about 10% or more, by about 20% or more, or by about 50% or more compared to the control level or reference value. The presence of a VOC marker which is absent in a control sample, is also contemplated as an increased level, deviation or change. The absence of a VOC marker which is present in a control, for example, is also contemplated as a decreased level, deviation or change.

Alternatively, the set of VOCs is characterized by a pattern which significantly differs from the patterns of said VOCs in control samples, or wherein the pattern is significantly different from a predetermined pattern of occurrence of VOCs.

The difference in the pattern can be analyzed with a pattern recognition analyzer which utilizes various algorithms including, but not limited to, principal component analysis, Fischer linear analysis, neural network algorithms, genetic algorithms, fuzzy logic pattern recognition, and the like. Exemplary algorithms are artificial neural networks, multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART) and statistical methods including, but not limited to, principal component analysis (PCA), partial least squares (PLS), multiple linear regression (MLR), principal component regression (PCR), discriminant function analysis (DFA) including linear discriminant analysis (LDA), cluster analysis including nearest neighbor, and support vector machine (SVM) analysis. Each possibility represents a separate embodiment of the invention.

Many of the algorithms are neural network based algorithms. A neural network has an input layer, processing layers and an output layer. The information in a neural network is distributed throughout the processing layers which are composed of nodes that simulate the neurons which are interconnected to the nodes. The analysis is performed by a series of vector matrix multiplications. Similar to statistical analysis which reveals underlying patterns in a collection of data, neural networks locate consistent patterns in a collection of data, based on predetermined criteria.

An exemplary pattern recognition algorithm is principal component analysis. Principal component analysis (PCA) involves a mathematical technique that transforms a number of correlated variables into a smaller number of uncorrelated variables. The smaller number of uncorrelated variables is known as principal components. The first principal component or eigenvector accounts for as much of the variability in the data as possible, and each succeeding component accounts for as much of the remaining variability as possible. The main objective of PCA is to reduce the dimensionality of the data set and to identify new underlying variables.

Principal component analysis compares the structure of two or more covariance matrices in a hierarchical fashion. For instance, one matrix might be identical to another except that each element of the matrix is multiplied by a single constant. The matrices are thus proportional to one another. More particularly, the matrices share identical eigenvectors (or principal components), but their eigenvalues differ by a constant. Another relationship between matrices is that they share principal components in common, but their eigenvalues differ. The mathematical technique used in principal component analysis is called eigenanalysis. The eigenvector associated with the largest eigenvalue has the same direction as the first principal component. The eigenvector associated with the second largest eigenvalue determines the direction of the second principal component. The sum of the eigenvalues equals the trace of the square matrix and the maximum number of eigenvectors equals the number of rows of this matrix.

An additional exemplary pattern recognition algorithm is discriminant function analysis (DFA). DFA is a linear, supervised pattern recognition method. The classes to be discriminated are defined before the analysis is performed. DFA determines the linear combinations of the measured values such that the variance within each class is minimized and the variance between classes is maximized. The DFA output variables (viz. canonical variables) are obtained in mutually orthogonal dimensions. The first canonical variable is the most powerful discriminating dimension, but the following canonical variables might also represent additional dimensions of differentiation. Thus, DFA effectively reduces the multidimensional experimental data, improves the human perception of the data and allows the distinction of clusters through visual perception of the first or the first and second canonical variables.

Yet another pattern recognition algorithm within the scope of the present invention is support vector machine (SVM) analysis. SVM analysis is a supervised learning method that provides the best separating line between two data sets through computerized analysis of the signal and automatic choice of the most suitable set of features. The method does not require normal distribution of the data points around the average value. The algorithm further provides comparison of subpopulations by building a multi-class classifier based on a linear nu-SVC SVM classifier.

The methods of the present invention are ex-vivo methods which comprise the use of any sample or specimen. Non-limiting examples of samples/specimens include a breath sample, a tissue sample, a serum sample, a urine sample, feces, a sweat sample, a vaginal discharge, a saliva sample and sperm. Each possibility represents a separate embodiment of the invention. In specific embodiments, the VOCs are measured directly through exposure to the sample. In other embodiments, the VOCs are measured through exposure to the headspace of a container in which the sample/specimen was placed. This measurement allows the diagnosis of fresh or on growing tissue/cells (e.g. in operating rooms). In certain embodiments, the sample/specimen is obtained from a tissue, for example a histological section.

In exemplary embodiments, the sample is a breath sample which may be tested as is, i.e. without a need for pre-concentration or dehumidification of the sample. Alternatively, the breath sample may be tested after being collected by a breath collector apparatus. Exemplary breath collector apparatus within the scope of the present invention are those approved by the American Thoracic Society/European Respiratory Society (ATS/ERS); (Silkoff et al., Am J Respir Crit. Care Med (2005) 171 912) for collecting alveolar breath. Alveolar breath is usually collected from individuals using the off-line method. However it is to be understood that breath collection directly to the device, vis-à-vis the on-line method is encompassed by the present invention. The breath collector apparatus may comprise a breath concentrator and/or a dehumidifying unit.

Breath concentrators that are within the scope of the present invention include, but are not limited to, solid phase microextraction (SPME) or sorbent tubes. The sorbent tubes are typically made of glass and contain various types of solid adsorbent material (sorbents). Commonly used sorbents include activated charcoal, silica gel, and organic porous polymers such as Tenax and Amberlite XAD resins. Sorbent tubes are attached to air sampling pumps for sample collection. A pump with a calibrated flow rate in ml/min draws a predetermined volume of air through the sorbent tube. Chemicals are trapped onto the sorbent material throughout the sampling period. This technique was developed by the US National Institute for Occupational Safety and Health (NIOSH). Within the scope of the present invention is cryogenic condensation which requires very low temperatures (typically less than −160° C.) to concentrate the VOCs.

Increasing VOC concentration may further be obtained by the use of a dehumidifier including, but not limited to, drawing moist air over cold refrigerated coils which condenses air moisture into droplets, silica gel (an amorphous form of silicon dioxide), activated carbon, and desiccant molecular sieves. Each possibility represents a separate embodiment of the invention. The breath collector apparatus may further comprise a heating/cooling unit, or a unit that monitors and stabilizes the conditions for sample maintenance (e.g. humidity, temperature, atmospheric pressure and the like).

The term "test subject" as used herein refers to a mammal, preferably a human subject. Currently preferred embodiments refer to human subjects who are at risk of developing lung cancer (e.g. smokers, individuals who have previously been treated for lung cancer and are at risk of recurrence of the disease). The methods of the present invention are applicable for deciding on a follow-up protocol by a physician and/or for referral to chemo-preventive therapy, to monitor therapy efficiency (during and after therapy-drug/surgery), to detect early recurrence after being cured and to diagnose fresh tissue (e.g. in operating rooms).

As used herein and in the appended claims the singular forms "a", "an," and "the" include plural references unless the content clearly dictates otherwise. Thus, for example, reference to "an organic coating" includes a plurality of such organic coatings and equivalents thereof known to those skilled in the art, and so forth. It should be noted that the term "and" or the term "or" are generally employed in its sense including "and/or" unless the content clearly dictates otherwise.

The principles of the present invention are demonstrated by means of the following non-limiting examples.

EXAMPLES

Example 1

GC-MS Measurements

Samples were analyzed with gas chromatography-mass spectroscopy (GC-MS; GC-6890N; MS-5975; Agilent Technologies Ltd.) combined with solid phase microextraction (SPME) as described in WO 2010/079491, the contents of which are incorporated by reference herein. Specifically, collected VOCs from test samples and from control samples were transferred to a stainless steel device. A manual SPME holder with an extraction fiber coated with Divenylbenzene/Carboxen/Polydimethylsiloxane (DVB/CAR/PDMS) (purchased from Sigma-Aldrich) was inserted into the stainless steel device for 20-30 minutes. The extracted fiber in the manual SPME holder was inserted into a GC injector which was set to 270° C. in the splitless mode. The oven temperature profile was: 40° C., held for 4 min, 5° C./min to 140° C., held for 4 min, 5° C./min to 250° C., held for 4 min. Capillary column H5-5MS 5% Phenyl Methyl Siloxane (30 m length, 0.25 mm i.d., 0.25 μm thickness) was used. The column pressure was set to 8.22 psi, and initial flow was 0.8 mL/min. Finally, the molecular structures of the VOCs were determined via the Standard Modular Set.

Example 2

Synthesis and Capping of Gold Nanoparticles and Sensor Fabrication

Gold nanoparticles having an average size of about 5 nm were capped with different organic molecules (4-methoxytoluenethiol, butanethiol, 3-methyl-1-butanethiol, 2-mercaptobenzoazole, and hexanethiol) as described in WO 2010/079490, the contents of which are incorporated by reference herein.

A sensors array of gold nanoparticles capped with the various organic coatings was fabricated as described in WO 2010/079490, the contents of which are incorporated by reference herein. In particular, functionalized gold nanoparticles having an average diameter of about 5 nm that were coated with 4-methoxytoluenethiol, butanethiol, 3-methyl-1-butanethiol, 2-mercaptobenzoazole, or hexanethiol, were dispersed in toluene by sonication, followed by a drop of the nanoparticles solution cast into the electrode. While still coated with solution, the substrate was blown with a stream of dry $N_2$. This process was repeated several times to yield the desired resistance, preferably from 20 KΩ to 5 MΩ. In other embodiments, film resistances from 100Ω to 80 MΩ) were prepared. The device was dried for 2 hours in a flume hood at an ambient temperature, and then heated to 50° C. in a vacuum oven over night.

The developed sensors were mounted onto a custom PTFE circuit board which had 40 separated sensor sites. The board was then mounted onto a stainless steel test chamber having a volume of less than 400 $cm^3$. An Agilent Multifunction switch 34980 controlled by USB was used to choose the active sensor and measure the corresponding resistance at a given time. The entire system was controlled by a custom Labview program.

Example 3

GC-MS Analysis of Cells

Figure 2:
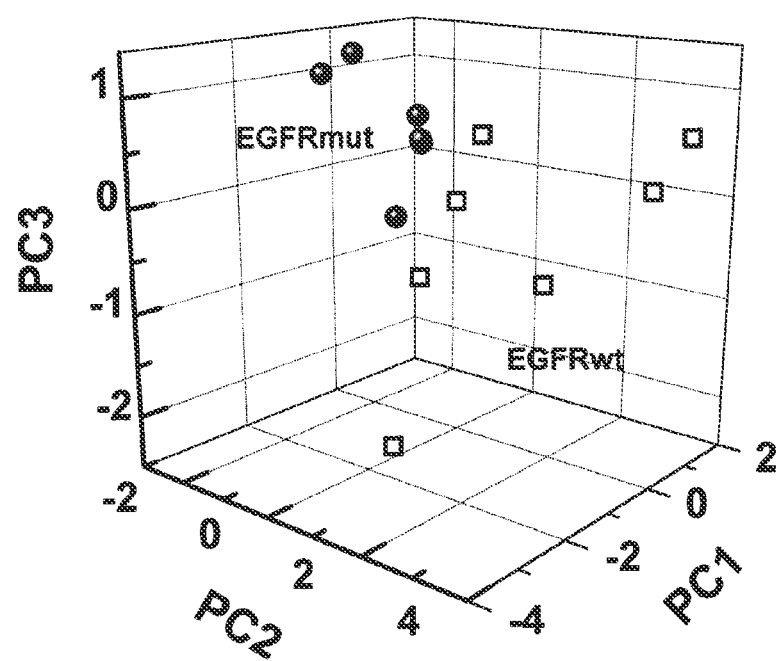
FIG. 2. PCA of the GC-MS multidimensional data set of cells having an EGFR mutation (●) and cells having wild type EGFR (□).

Non-Small Cell Lung Cancer (NSCLC) with or without EGFR mutations were analyzed using GC-MS in order to determine which volatile organic compounds are indicative of EGFR mutations. FIG. 1 shows the average abundance ratio of the VOCs as identified using the SPME technique in combination with GC-MS. The values presented in the figure were calculated after subtracting the mean amount of the medium on which the cells were grown. Compounds having a signal >0.02% of the total amount are presented. PCA analysis was performed for compounds with the largest difference in abundance between cells with EGFR mutants and cells with wild type EGFR. The compounds were chosen such that no overlap between the error bars of the two groups occurred. The first three principal components depicted contained >90% of the total variance in the data. (FIG. 2).

Example 4

Sensor Analysis of Cells

Figure 3:
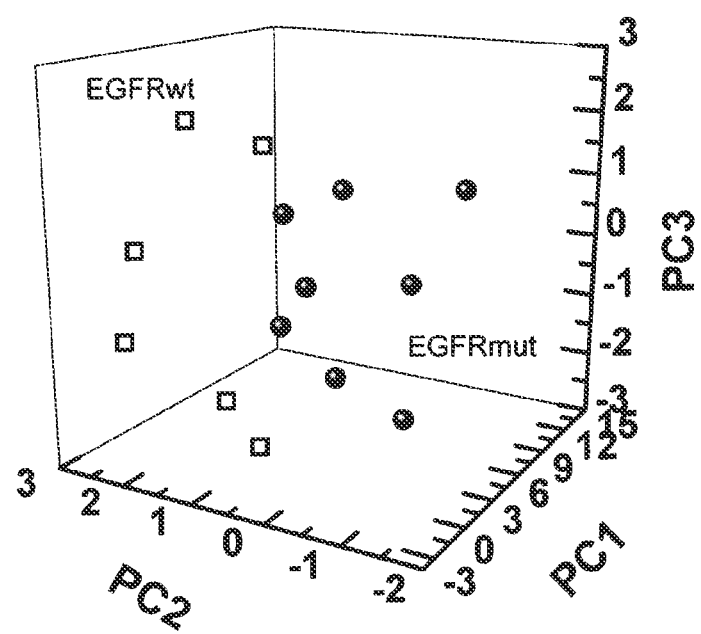
FIG. 3. PCA of the gold nanoparticles multidimensional data set of cells having an EGFR mutation (●) and cells having wild type EGFR (□).

The sensing of VOCs from EGFR mutant and wild type cells was examined using the sensor array of Example 2 combined with PCA analysis. FIG. 3 shows well-defined clusters of the two states except for one misclassification. The results presented imply on fast and reliable examination of the two genetic states of lung cancer.

Figure 4:
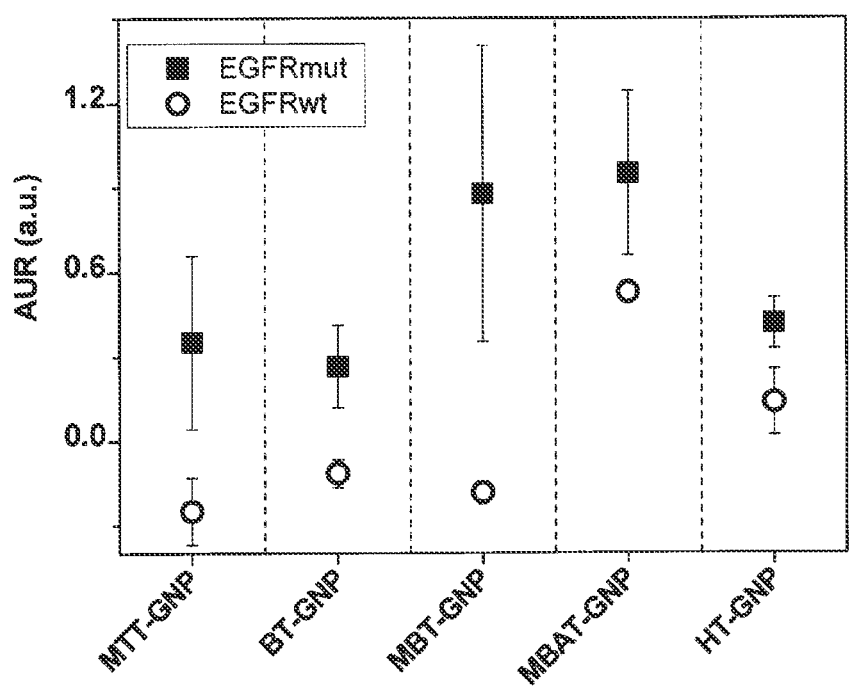
FIG. 4. The area under response (AUR) of selected sensors of gold nanoparticles capped with various organic coatings to VOCs of cells having an EGFR mutation (■) and cells having wild type EGFR (○).

FIG. 4 shows a representative example for pre-selection of sensors of gold nanoparticles capped with various organic coatings input data (area under response; AUR). Suitable sensors for distinguishing between cells with EGFR mutation (EGFRmut) and cells with wild type EGFR (EGFRwt) were selected if the variances (error bars) obtained for the different states from the entire cell population did not overlap. The sensors that were used: 4-Methoxytoluenethiol-capped gold nanoparticles (MTT-GNP), Butanethiol-capped gold nanoparticles (BT-GNP), 3-Methyl-1-butanethiol-capped gold nanoparticles (MBT-GNP), 2-Mercaptobenzoazole-capped gold nanoparticles (MBAT-GNP), and Hexanethiol-capped gold nanoparticles (HT-GNP). The figure shows clear differences between the sensing signals obtained for the two states.

Figure 5:
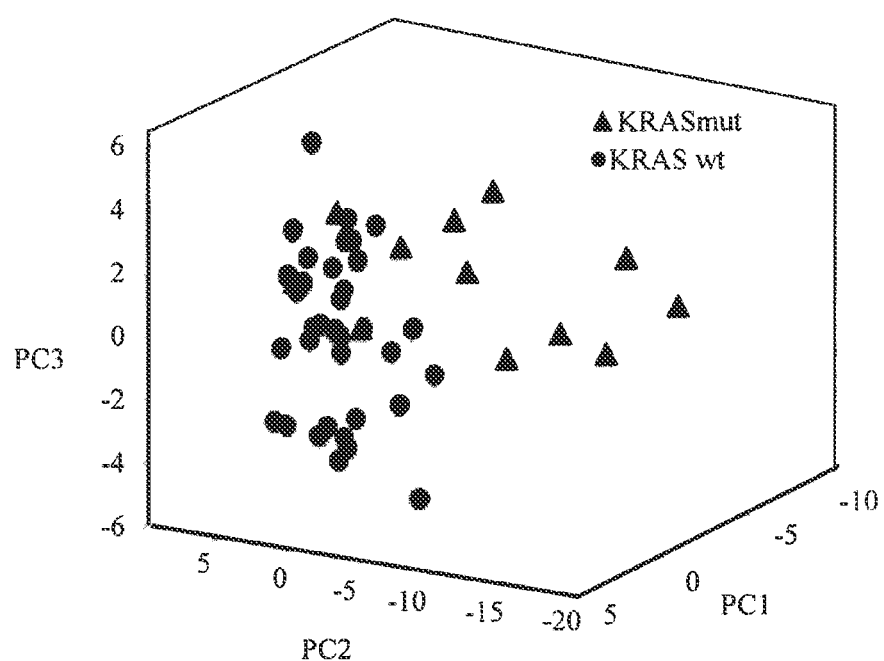
FIG. 5. PCA of the gold nanoparticles multidimensional data set of cells having a KRAS mutation (▲) and cells having wild type KRAS (●).

Selective sensors of gold nanoparticles capped with various organic coatings were further used to differentiate between cells with KRAS mutations and cells with wild type KRAS. FIG. 5 shows the differentiation between the two populations following PCA analysis. Well separated populations are seen.

Example 5

Sensor Analysis of VOCs from the Headspace of Cancerous Lung Cells

Figure 6:
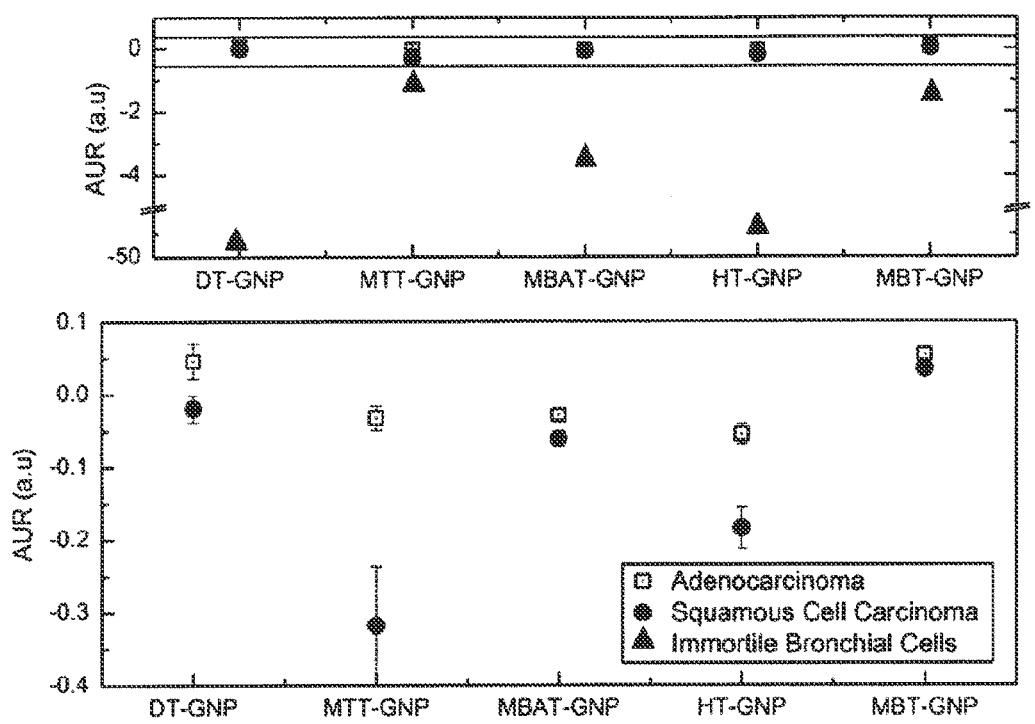
FIG. 6. A representative example for pre-selection of gold nanoparticles sensors input data (area under response; AUR) for differentiation between adenocarcinoma cells (⊡), squamous cell carcinoma (●), and immortal bronchial cells (▲).

The sensing of VOCs from the headspace of a container with small-cell lung cancer (SCLC), non-SCLC(NSCLC) or sub-types of NSCLC was examined using a sensor array of gold nanoparticles capped with various organic coatings combined with PCA analysis. Twelve NSCLC cell lines, sub-categorized to eight adenocarcinoma NSCLC cell lines (A549, Calu-3, H820, H1435, H1650, H1975, H4006, H2009), four squamous NSCLC (H226, HCC15, HCC95, NE18) and 4 SCLC cell lines (H69, H187, H526, H774) were grown in duplicates in 100 mm cell-culture dish from seeding ($\sim 2\times 10^6$ cells) up to 95% confluency ($7\times 10^6$ cells), using two dimensional medium in standard conditions (RPMI 1640 medium+10% FBS; 5% $CO_2$ environment). The medium for the same incubation time and conditions but without cells served as a baseline (background) control in duplicates. In addition, normal immortalized bronchial epithelial cells (MINA 3KT) were grown (in seven repetitions) using BEBM medium (BEBM+BEGM SingleQuots (Cat 4175) by Lonza (Walkersville, Md., USA) as another reference control. The medium for the same incubation time and conditions but without cells served as a control in duplicates for the bronchial epithelial cells. Each cell culture was placed in a bigger dish (15 mm in diameter) and two Ultra II SKC™ badges with Tenax TA as a sorbent (265 mg; SKC Inc) were placed next to it for absorbing the headspace atmosphere during the total growth time (median time 68 hours (range 60-72 hr)). At end of the headspace collection process, the Tenax was transferred to a thermal desorption device for extracting the sorbed VOCs. The extracted VOCs were fed into the electronic nose system without any further treatment. The analysis was performed as follows: five minutes of vacuum were followed by 5 minutes of sample exposure; this procedure was repeated 3 times to get 3 cycles for each sample. The sensing signals were normalized by the equivalent empty medium (RPMI 1640 medium+10% FBS), collected before or after each lung cancer cell line sample, to account for possible (natural) drifts or fluctuations in the sensors. FIG. 6 shows that different cell lines produce measurable changes in the responses of the individual gold nanoparticle chemiresistors. Every sensor in the array underwent a rapid and fully reversible change in the electrical resistance when exposed to the headspace sample. Some of the sensors showed positive resistance changes (e.g., 3-Methyl-1-butanethiol-capped gold nanoparticles; MBT-GNP) and others showed negative resistance changes (e.g., 4-Methoxytoluenethiol-capped gold nanoparticles; MTT-GNP, 2-Mercaptobenzoazole-capped gold nanoparticles; MBAT-GNP, and Hexanethiol-capped gold nanoparticles; HT-GNP) for all examined cell types. Exceptional to these trends were sensors that showed positive resistance change to specific types of lung cancer cells, yet negative resistance to other cell types (e.g., Dodecanethiol-capped gold nanoparticles DT-GNP). Sensors that were selected for further analysis were sensors that exhibited no overlap between their variances (or error bars) upon exposure to different cell types. The entire samples participated in this study.

Figure 7:
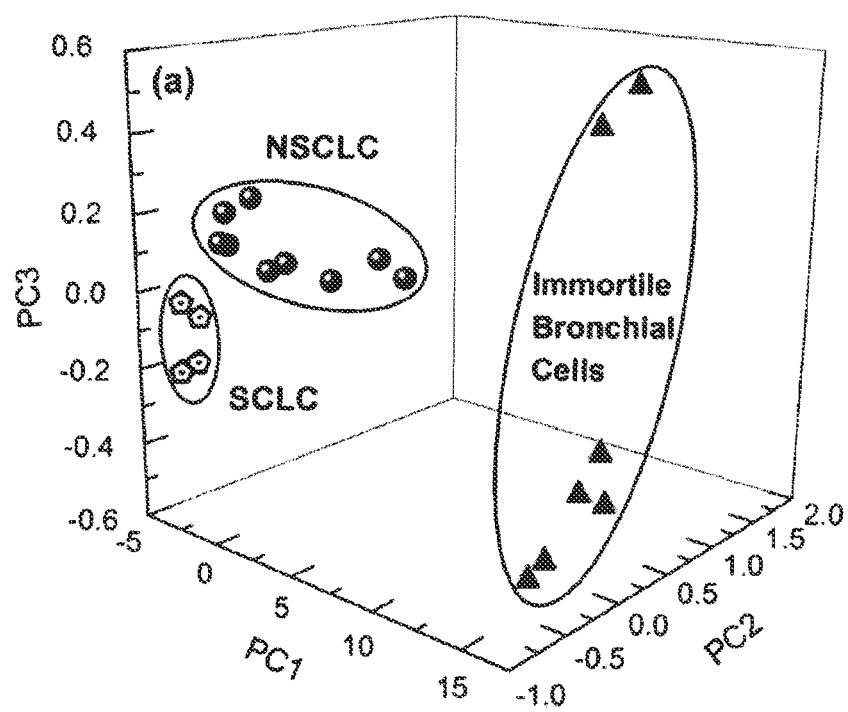
FIG. 7. PCA of the gold nanoparticles multidimensional data set of NSCLC (●), SCLC (pentagons) and immortal bronchial cells (▲) (p<0.001).
Figure 8:
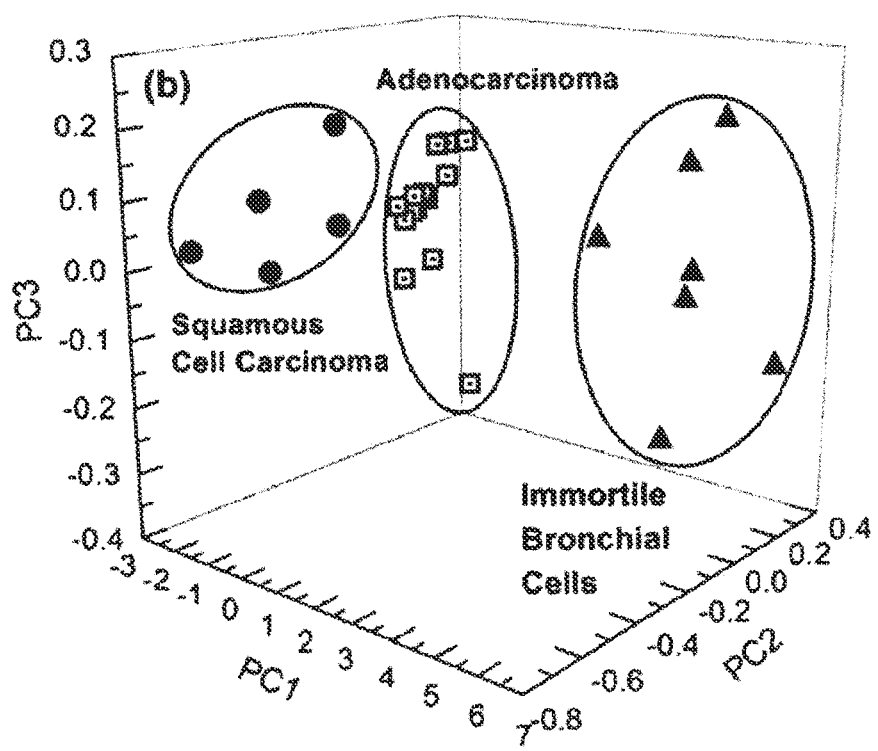
FIG. 8. PCA of the gold nanoparticles multidimensional data set of sub-categories of NSCLC (squamous cell carcinoma (●) and adenocarcinoma (▫) and immortal bronchial cells (▲)(p<0.003).

In order to analyze all data outputs, a multi-dimensional approach was taken using principal component analysis (PCA). FIG. 7 shows excellent separation (p<0.001) was achieved in principal component space between the patterns of immortal bronchial cells and lung cancer cells (both SCLC and NSCLC). As a qualitative measure of this separation, 20 units in the PC1 axis were observed between the immortal bronchial cells and SCLC/NSCLC states. The clusters of the SCLC and NSCLC were closer, yet clearly separated, from each the other (p<0.003). The best separation between these two clusters was obtained on the PC2 axis, which exhibited ~0.8 units' difference, while the separation at the PC1 and PC3 scales was ~0.2-0.4 units. In order to account for the enriched medium in which the immortal bronchial cells were grown, the background signals for each of the experiments was subtracted from the signal obtained from the medium. In addition to the separation between SCLC and NSCLC, a clear differentiation was obtained between subtypes of NSCLC (p<0.003), adenocarcinoma and squamous cell carcinoma (~0.6 units on the PC2 and ~0.1-0.2 units on the PC1 and PC3 axis) and when compared to immortal bronchial cells (~8 units on the PC1 axis) (FIG. 8). It should be noted that the clusters in these two states were more scattered (~15-20%) than those obtained in the SCLC and NSCLC cases. Without being bound by any theory or mechanism of action, this could be attributed to higher similarity in the chemical compositions between the subcategories of NSCLC, as compared to the situation between SCLC and NSCLC.

Example 6

GC-MS Analysis of VOCs from the Headspace of Cancerous Lung Cells

Figure 9A:
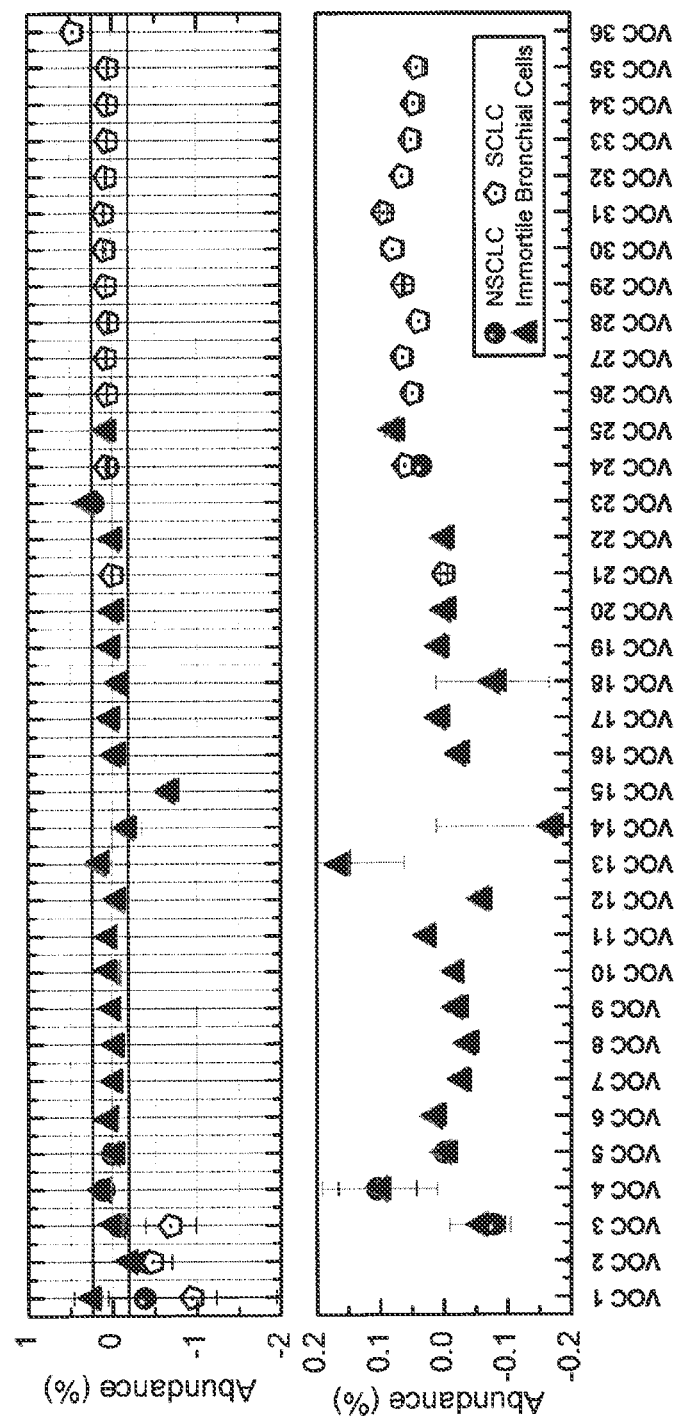
FIGS. 9A-9B.

The VOC composition of the headspace of a container with small-cell lung cancer (SCLC), non-SCLC (NSCLC) or subtypes of NSCLC was measured using GC-MS analysis after pre-concentration process via solid phase microectarction (SPME). When comparing cancer to immortal normal bronchial cells, only net signals (subtracting all background) were analyzed. The GC-MS/SPME analysis identified over 1000 different VOCs in each headspace sample. The VOCs that were chosen for analysis were the ones with >0.02% of the total amount detected by GC-MS. In order to test which VOCs were statistically significant for the analysis, step forward analysis was performed in two main modes: (i) The VOC levels which changed in >80% of the cell lines (SCLC, NSCLC and healthy states) and in >80% of the equivalent medium control were referred to as non-statistically significant; and (ii) The VOC levels which changed in >80% of the lung cells (SCLC, NSCLC and healthy states) and in <20% of the equivalent medium control were referred to as statistically significant. The results of these analyses are summarized in FIG. 9A where ~93% of the VOCs resealed by the cancer cells were hydrocarbons, methylated hydrocarbons, benzene derivatives, aldehydes, ketones and alcohols. Specifically the VOCs resealed by the cancer cells: VOC 1=styrene; VOC 2=benzaldehyde; VOC 3=phenol; VOC 4=toluene; VOC 5=octanal; VOC 6=isopropyl myristate; VOC 7=2-undecanone; VOC 8=decanal; VOC 9=1-dodecene; VOC 10=undecanal; VOC 11=decane: VOC 12=nonanal: VOC 13=hexadecane; VOC 14=tridecane; VOC 15=tetradecane; VOC 16=N,N-dibutylformamide; VOC 17=3-methyl undecane; VOC 18=1,3-bis(1,1-dimethyl)benzene; VOC 19=acetophenone; VOC 20=2-methyl dodecane; VOC 21=1,4-dimethyl-2,5-cyclohexadiene; VOC 22=3-methyl tridecane; VOC 23=2-ethyl-1-hexanol; VOC 24=4-methyl tetradecane; VOC 25=2-methyl hexadecane; VOC 26=7-methyl tridecane; VOC 27=5-methyl-2-(1-methylethyl)-1-hexanol, acetate; VOC 28=2,5-dimethyl dodecane; VOC 29=(S)-(+)-5-methyl-1-heptanol; VOC 30=2,2,4-trimethyl pentanenitrile; VOC 31=acetic acid octyl ester; VOC 32=4-methyl-1-heptanol; VOC 33=N-butyl benzenesulfonamide; VOC 34=pentylcyclopentane; VOC 35=5-methyl-1-heptanol; and VOC 36=2,4-dimethyl undecane. NSCLC, SCLC and healthy states released/consumed styrene, benzaldehyde and phenol at different abundances, as expressed via the relative abundance values in the figure. Toluene and 2-ethyl-1-hexanol were released by both NSCLC and the immortal bronchial cells but not by the SCLC. SCLC released additional 12 VOCs that were not released by the NSCLC cells and were not found in their medium as well. Those VOCs are mainly branched hydrocarbons and alcohols, but include also an organic acid and its ester. In addition, 17 VOCs were either consumed or released by the immortal bronchial cells and were not observed in the cancerous cells at all (normalized for the type of medium).

Figure 9B:
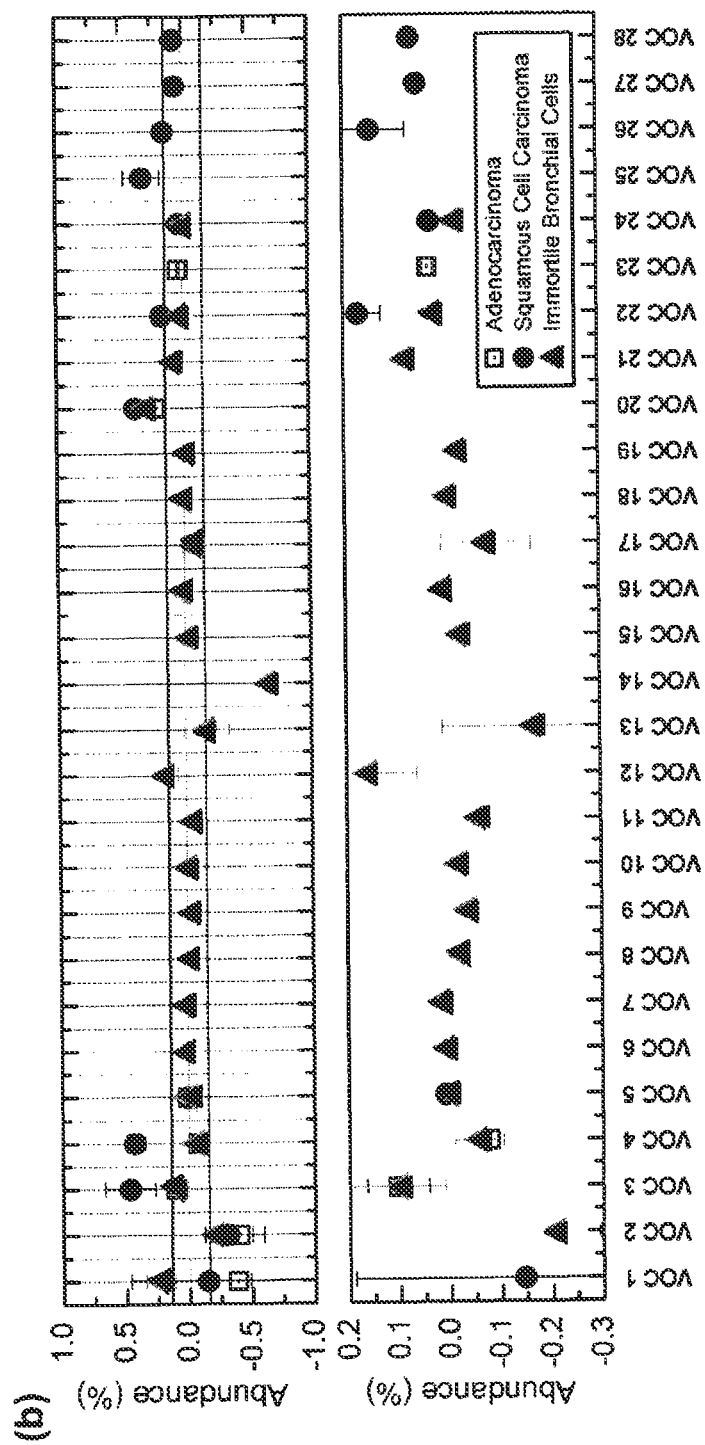

Examining the sub-categories of the NSCLC (FIG. 9B) showed that styrene, benzaldehyde, 2-ethyl-1-hexanol, toluene and phenol are all common to adenocarcinoma, squamous cell carcinoma and healthy states, yet appear at different concentrations. Phenol is the only VOC that is being produced by squamous cell carcinoma but consumed by adenocarcinoma. 6 VOCs were found to be produced by squamous cell carcinoma but do not appear in adenocarcinoma cells at all. 16 VOCs are either produced or consumed by healthy states and not by the cancer cells. VOC 1=styrene; VOC 2=benzaldehyde; VOC 3=toluene; VOC 4=phenol; VOC 5=octanal; VOC 6=acetophenone; VOC 7=isopropyl myristate; VOC 8=2-undecanone; VOC 9=decanal; VOC 10=1-dodecene; VOC 11=nonanal; VOC 12=hexadecane; VOC 13=tridecane; VOC 14=tetradecane; VOC 15=N,N-dibutylformamide; VOC 16=3-methyl undecane; VOC 17=1,3-bis(1,1-dimethy)benzene; VOC 18=2-methyl dodecane; VOC 19=3-methyl tridecane; VOC 20=2-ethyl-1-hexanol; VOC 21=2-methyl hexadecane; VOC 22=decane; VOC 23=4-methyl tetradecane; VOC 24=undecanal; VOC 25=triethylamine; VOC 26=α,α-dimethyl benzenemethanol; VOC 27-=hexadecanenitrile; and VOC 28=6,10-dimethyl-5,9-undecadien-2-one.

Figure 10:
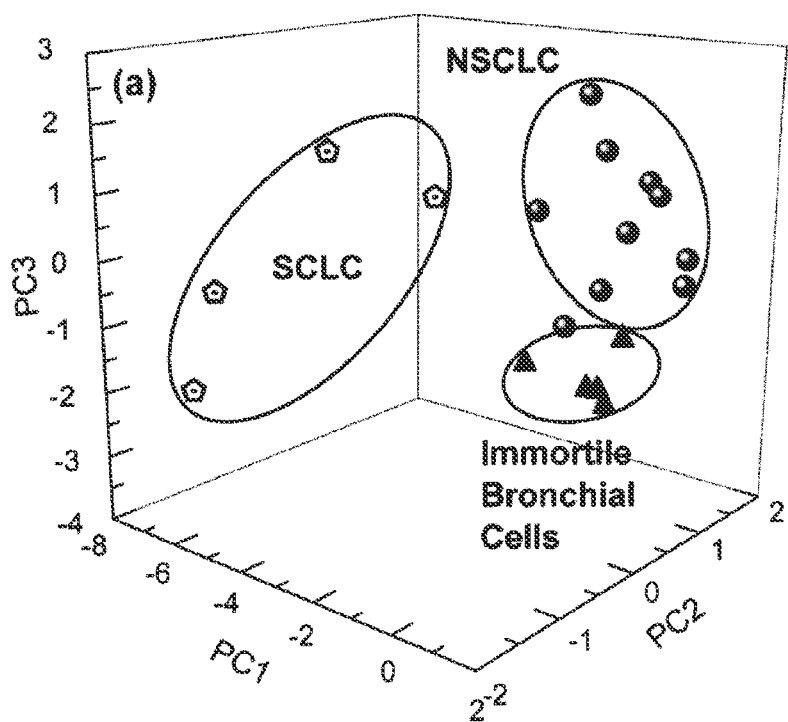
FIG. 10. PCA of the GC-MS analysis of immortal bronchial cells (▲), SCLC (pentagons), and NSCLC (●).

PCA analysis that was carried out for the GC-MS multidimensional data set, using only VOCs that have shown clear differences in the various diseases states was performed. The best discrimination was based on VOCs that their variance (error bars) showed no overlap with each other. As could be seen in FIG. 10, a good separation was obtained between the SCLC and NSCLC cells, but not between the NSCLC and immortal bronchial cells.

Example 7

Breath Collection

Exhaled breath was collected in a controlled manner from 12 volunteers at the ages of 51-78. The volunteers were patients having lung cancer at stages 1-4, subjects having dysplasia at various stages and healthy subjects. The ratio between male-to-female volunteers was ~5:1. Nine volunteers out of 12 were ex-smokers and three volunteers were active smokers. These patients were classified as being at high-risk for developing cancer due to family history, smoking history, etc. Inhaled air was cleared of ambient contaminants by repeatedly inhaling to total lung capacity for 5 minutes through a mouthpiece (purchased from Eco Medics) that contained a filter cartridge on the aspiratory port, thus removing more than 99.99% of the exogenous VOCs from the air during inspiration. Immediately after lung washout, the subjects exhaled through a separate exhalation port of the mouthpiece against 10-15 cm $H_2O$ pressure to ensure closure of the vellum to exclude nasal entrainment of gas. Exhaled breath contained a mixture of alveolar air and respiratory dead space air. Subjects exhaled into the breath collector which automatically filled the dead space air into a separate bag and the alveolar breath into a 750 ml Mylar sampling bag (polyvinyl fluoride, purchased from Eco Medics) in a single-step process. The Mylar bags were re-used and thoroughly cleaned prior to each use with flowing $N_2$) (99.999% purity) for 5-8 minutes (GC-MS in conjugation with pre-concentration techniques showed that this purification process eliminates >99% of the contaminants and/or VOCs from the Mylar bags). At least two bags were collected from each individual for subsequent analysis. All bags were analyzed within two days from the time of breath collection to assure accuracy of the results.

Example 8

Principle Component Analysis of Breath Samples

The responses of the sensor array to the breath samples of healthy subjects, subjects having lung cancer (pre-surgical) and subjects with dysplasia were analyzed using principle component analysis (PCA). Each data point corresponds to the multidimensional $\Delta R/Rb$ and $\Delta R$ (where Rb is the baseline resistance of the sensor in the absence of analyte and $\Delta R$ is the baseline-corrected steady-state resistance change upon exposure of the sensor to analyte) of one breath sample and is then averaged response of 3 exposures.

Figure 11:
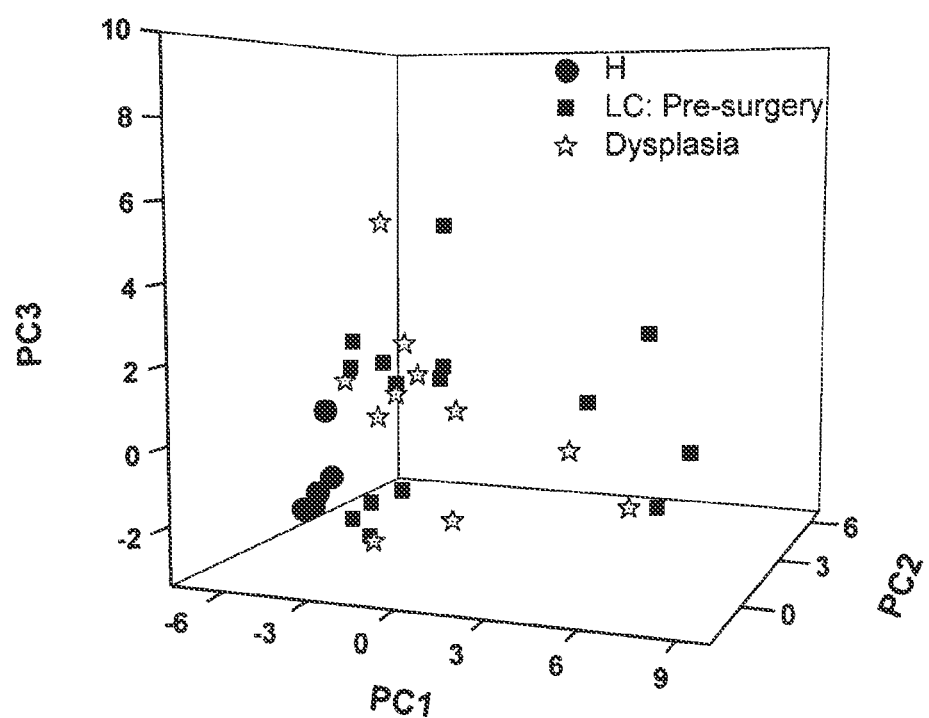
FIG. 11. PCA of the data set of breath samples of healthy subjects (H; ●), pre-surgical lung cancer patients (LC; ■) and subjects having dysplasia (stars).
Figure 12:
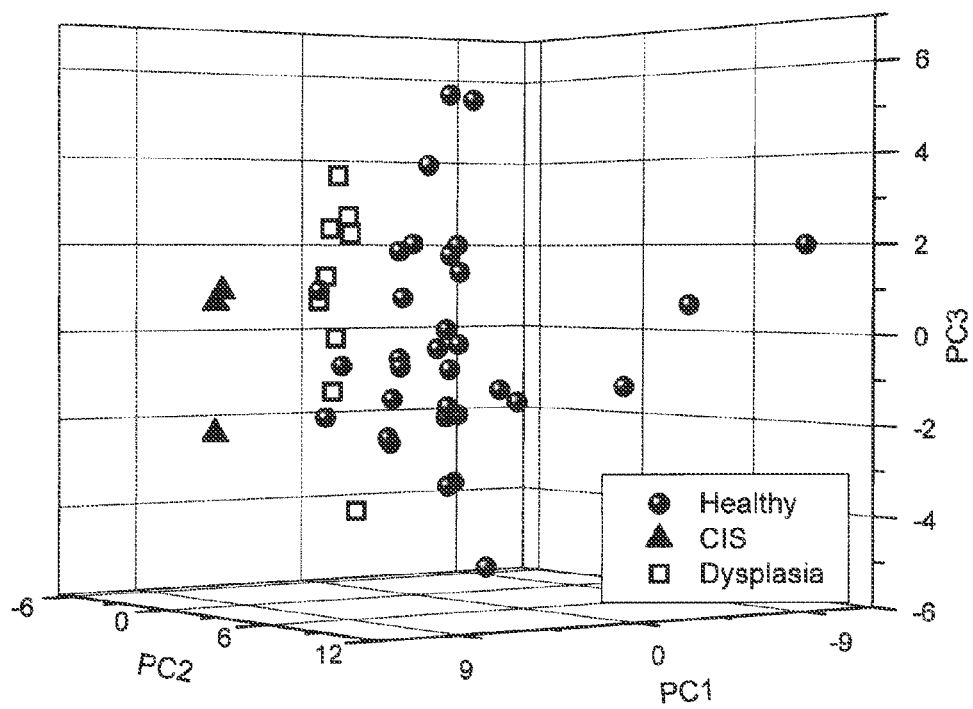
FIG. 12. PCA of the dataset of breath samples of healthy subjects (●), pre-surgical lung cancer patients (carcinoma in situ; CIS; ▲) and subjects having dysplasia (□) which was run in the electronic nose apparatus during a period of one month.

A good separation was obtained between the pre-surgical lung cancer patients and healthy subjects (FIG. 11). However, subjects having dysplasia states, exhibited signals that overlapped with those obtained from lung cancer patients at stages 1-4. The main overlap was near the border line of healthy subjects and the lung cancer patients. Thus, the concentration of the VOCs is elevated even when histological changes begin to occur in the lung cells. FIG. 12 shows the PCA analysis of breath samples of 11 healthy subjects, 3 subjects with dysplasia and 1 subject with carcinoma in situ (CIS). The breath samples were tested during a period of one month to insure negligible sensor drift. PC1 values differentiate between healthy and dysplasia subjects. The points assigned to the patient having carcinoma in situ show higher PC1 values.

Figure 13:
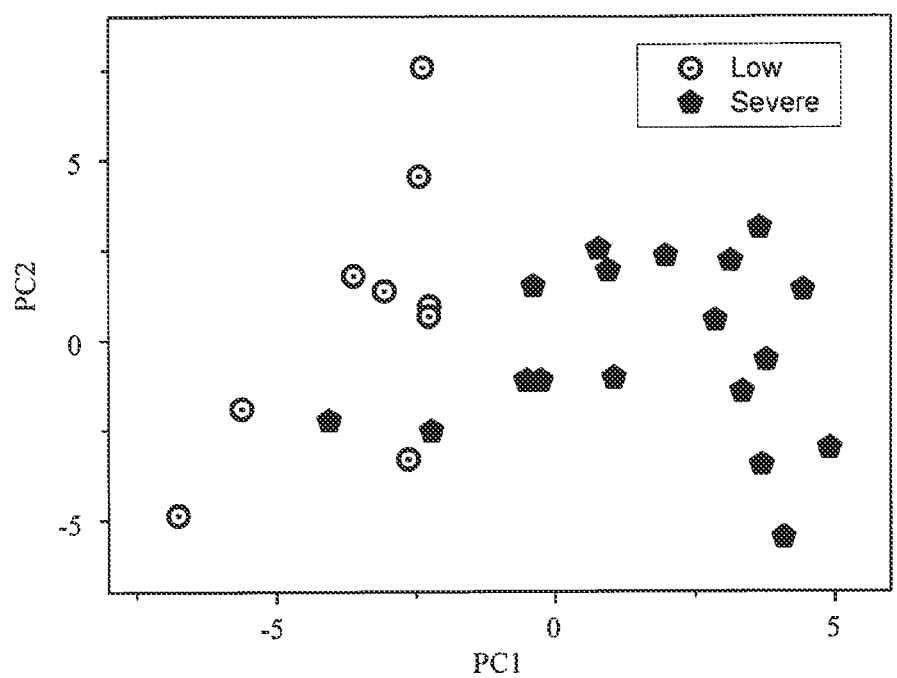
FIG. 13. PCA of the dataset of low grade (⊚) and severe (✺) dysplasia patients.

FIG. 13 shows the PCA analysis of subjects with various stages of dysplasia. Six samples were obtained from subjects with severe dysplasia and 3 samples were obtained from subjects with low grade dysplasia. PC1 represents the maximum variance between the groups showing good separation of the two populations. The two points of misclassification were obtained from the same subject.

It is therefore concluded that the electronic nose apparatus differentiates between dysplasia states, healthy states and lung-cancer states, and further differentiates between different stages of dysplasia states.

Example 9

GC-MS Analysis of Breath Samples

A representative number of breath samples were analyzed using GC-MS in order to determine which volatile organic compounds are indicative of dysplasia. Six dysplasia samples were thus compared to 5 healthy samples and 5 lung cancer samples.

Although the majority of the analyzed VOCs were found in all three groups (lung cancer, dysplasia and healthy) in more than 80% of the samples, a set of VOCs was found at significantly different concentrations in each of the groups. For example, the area under the GC-MS peak of 4-hydroxy-4-methyl-2-pentanone decreased in average by 17.5% in dysplasia samples and increased in average by 34% in lung cancer samples, in comparison to the mean area of the same compound in healthy samples. Similar behavior was detected for other VOCs including decanal, 2,4-dimethyl-heptane, ethylbenzene, styrene, 1-ethyl-3-methyl benzene, butyrolactone, octane, 5-hepten-2-one, 6-methyl acetic acid, 2-ethylhexyl ester, 4-ethyl-heptane, pentadecane, 3-methyl-tetradecane, tridecane, and d-limonene.

Figure 14:
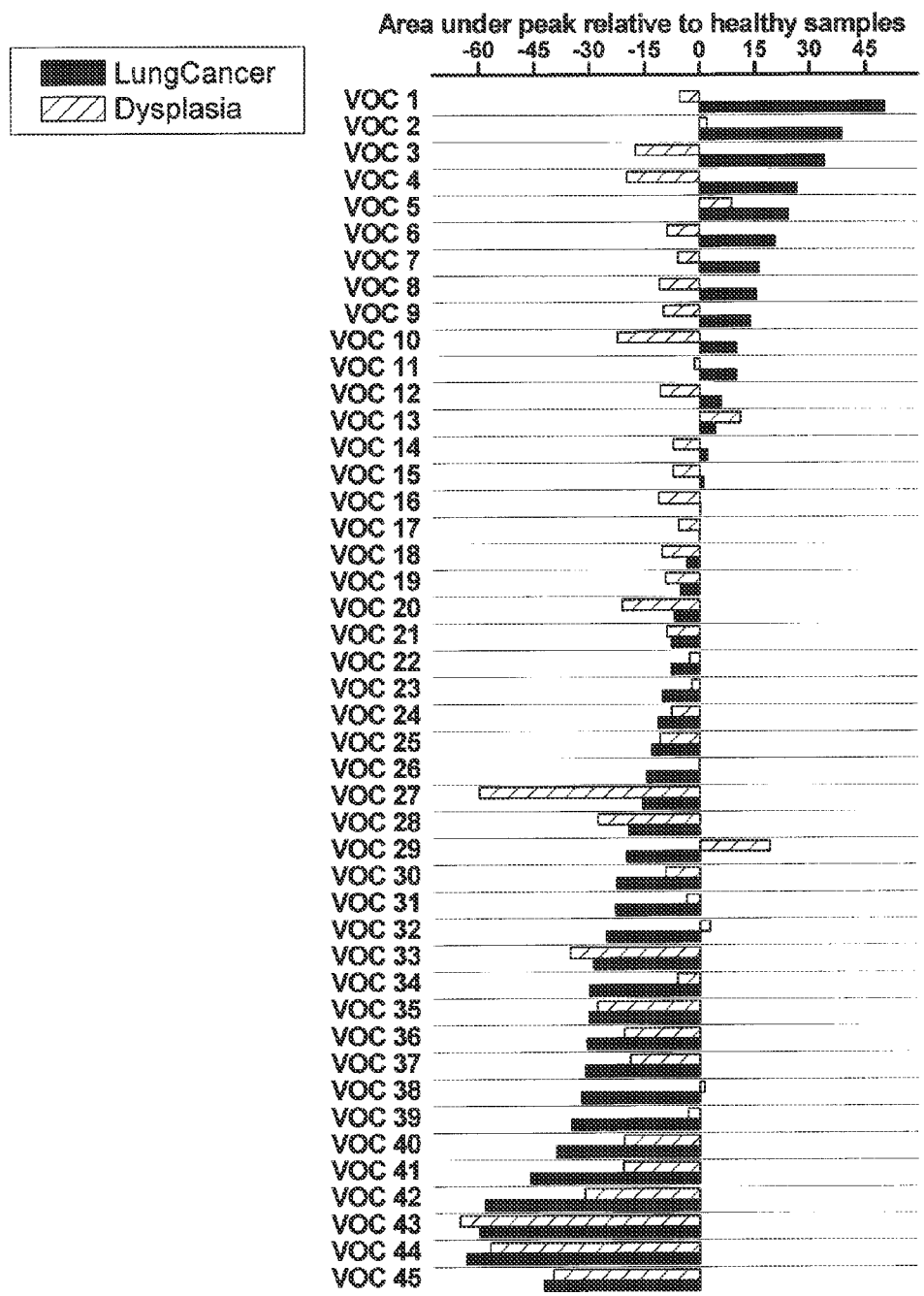
FIG. 14. GC-MS analysis of breath samples of subjects having dysplasia (normalized to healthy subjects) and samples from lung cancer patients (normalized to healthy subjects).

FIG. 14 shows the average abundance ratio of the VOC values as determined by GC-MS combined with SPME. VOC 1=2,4-dimethyl heptane; VOC 2=pentadecane; VOC 3=4-hydroxy-4-methyl-2-pentanone; VOC 4=ethylbenzene; VOC 5=1,2,3-trichloro-benzene; VOC 6=1-ethyl-2-methyl-benzene, VOC 7=3-carene; VOC 8=1-ethyl-3-methyl-benzene; VOC 9=styrene; VOC 10=o-xylene or p-xylene or 1,3-dimethyl-benzene; VOC 11=decanal; VOC 12=dodecane; VOC 13=acetophenone; VOC 14=1,2,3-trimethyl-benzene; VOC 15=2,4-hexadiyne; VOC 16=3-chloropropionic acid or 2-tetrahydrofurylmethyl ester or 2-bromoethyl-oxirane or 2,3,4-trimethyl-decane; VOC 17=D-limonene; VOC 18=chlorobenzene; VOC 19=propylbenzene; VOC 20=1-ethenyl-4-methyl-benzene; VOC 21=Bicyclo[2.2.2]octan-1-ol or trans-2-methyl-4-n-pentylthiane or S,S-dioxide or [6-cyclopentyl-3-(3-cyclopentylpropyl)hexyl]-cyclohexane; VOC 22=benzaldehyde; VOC 23=methyl ester hexadecanoic acid; VOC 24=6-methyl-5-hepten-2-one; VOC 25=propylcyclohexane; VOC 26=octane; VOC 27=4-ethyl-heptane; VOC 28=isopropyl myristate; VOC 29=butyrolactone; VOC 30=2-ethylhexyl ester acetic acid; VOC 31=1-bromo-4-(trifluoromethyl)-benzene; VOC 32=1-methylethyl ester dodecanoic acid; VOC 33=2,4,6-trimethyl-octane; VOC 34=methoxybenzene; VOC 35=2-methyl-propanoic acid or 1-(1,1-dimethylethyl)-2-methyl-1,3-propanediyl ester; VOC 36=decyl-cyclopentane; VOC 37=5-butylnonane; VOC 38=tridecane; VOC 39=heptanal; VOC 40=2,5-dimethyloctane; VOC 41=3-methyltetradecane; VOC 42=2,2,3,3,5,6,6-heptamethyl-heptane or 6-methyl-pentadecane; VOC 43=1,2-benzenedicarboxylic acid or bis(2-methylpropyl)ester; VOC 44=tricosane-2,4-dione or 2,4-imidazolidinedione or 5-(2-methylpropyl)- or 4-octadecyl-(S)-morpholine or 6-undecylamine; VOC 45=toluene. The set of VOCs indicative of dysplasia includes main mass: 57 which eluted in retention time of 28 min. This corresponds to 6-ethyl-undecane, 2,6-dimethyl-octane, 2,6-dimethyl-heptadecane, 3-(bromomethyl)-heptane, 5-(2-methylpropyl)-nonane, 3-methylnonane, or 4,6-dimethyl-dodecane.

The volatile organic compounds detected in at least 80% of the breath samples of the healthy population and lung cancer patients but not detected in the majority of the breath samples of dysplasia includes 2-heptanone, undecane, heptadecane, 2,4-hexadiene, 2,2,3-trimethyl-cyclohexane, 3,7-dimethyl-2-octene, 3,3,5-trimethyl-cyclohexanone, 1-chloro-decane, borneol, 1,2,3,4-tetrahydro-naphthalene, and 4,9,9-trifluoro-bicyclo[6.1.0]nona-2,4,6-triene.

Example 10

GC-MS Results of EGFR Mutations and Dysplasia

A comparative analysis, of the GC-MS results, was performed for the Non-Small Cell Lung Cancer (NSCLC) with EGFR mutations and breath samples of dysplastic patients. Only 6 VOCs were found in more than 80% of the samples from each group: (1) benzaldehyde; (2) styrene; (3) toluene; (4) tridecane; (5) isopropyl myristate and (6) undecane. These are prevalent volatiles in the breath since they also appear in healthy subjects and lung cancer patients. The majority of detected VOCs are distinctive of each of the groups. For example: 4-methyl 1-heptanol, 2-ethyl-1-hexanol, acetic acid octyl ester, decane; 3-methyl-decane, octanal, pentadecanenitrile and tetradecene are VOCs which appear in >80% of cells containing EGFR mutations and not in dysplastic subjects. On the other hand: 2,4-hexadiyne, 2-heptanone, 3,7-dimethyl-2-octene (Z) or 2-hexyl-1,1,4-trimethyl-cyclobutane or 2-methyl-bicyclo[2.2.2]octan-1-ol, 4-hydroxy-4-methyl-2-pentanone, 6-methyl-5-hepten-2-one, 2-ethylhexyl ester acetic acid, acetophenone; 1,2,3-trichloro-benzene, 1,2,3-trimethyl-benzene, butyrolactone, decanal, d-limonene, dodecane, ethylbenzene, heptadecane or octadecane, 5-butyl-nonane, pentadecane, 2-methyl-propanoic acid, and 1-(1,1-dimethylethyl)-2-methyl-1,3-propanediyl ester are part of the VOCs that were found in >80% of the dysplasia samples and not in the EGFR mutational cells.

Example 11

Cell Culture and Headspace Sampling

Commercially available cell lines with long term gene and expression analysis were obtained from the Colorado cell bank registry (Table 1). The cell lines were grown in a 100-mm cell-culture dish to 95% confluency over 3 days ($7 \times 10^6$ cells) using a standard medium (RPMI 1640 medium 10% fetal bovine serum; 5% $CO_2$ environment). A medium with the same incubation time and conditions but without cells served as a control. The headspace volatile biomarkers were collected during the incubation time using two ULTRAII SKC™ passive sampling badges containing Tenax TA (265 mg; SKC Inc) as a sorbent material. The sorbent material that was exposed to the headspace of the cell cultures or the empty medium was transferred to a thermal desorption device made of stainless steel that was pre-heated to 270° C.

to the breath samples in the middle and at the end of the signal. The classification success rate of the binary problems was estimated through leave-one-out cross validation. For this purpose, DFA was computed using a training data set that excluded one test sample. After the DFA computation, the test sample was projected onto the CV1 axis that was calculated using the training set. Thereby the test sample was "blinded" against the DFA model, so that its class affiliation was unknown. All possibilities of leaving out one sample were tested and the left out sample was classified as true positive (TP), true negative (TN), false positive (FP) and false negative (FN).

Figure 15A:
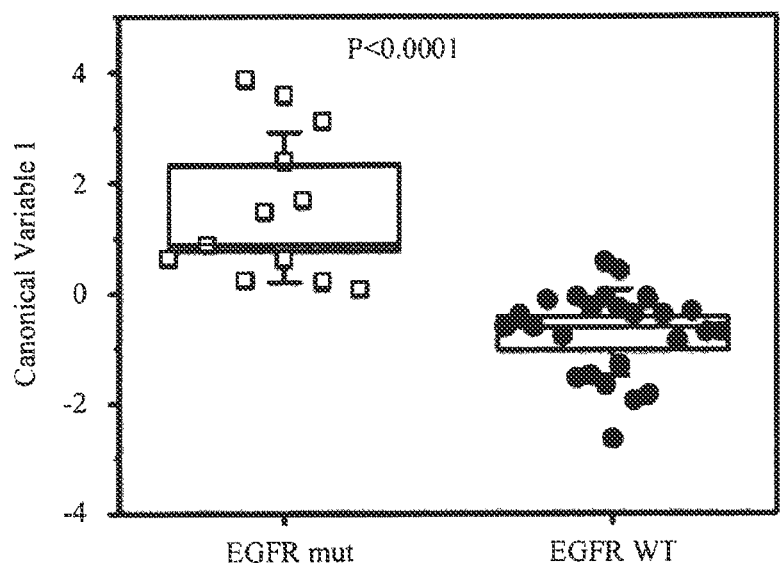
FIGS. 15A-15I. DFA plots of the first canonical variable (CV1) that was calculated from the responses of 2-4 sensors of organically functionalized gold nanoparticles to the headspace samples of NSCLC cell lines having EGFR and KRAS mutations, ALK fusion genes and NSCLC cell lines that are wild type (WT) to the three mutations (mut).

The VOC signature of EGFR and KRAS mutations, as well as ALK fusion genes from selected signals of the four gold nanoparticle (GNP) sensors was identified. The headspace samples of several cell lines (i.e., the gaseous constituents of a closed space above the cell lines) with specific well defined genetic mutations (10 EGFR mutations, 14 KRAS mutations, and 8 ALK fusion genes) were compared. A small group of 5 samples from lung cancer cell lines which are wild type (WT) to all three mutations of interest was included as an additional control group. FIG. 15A shows that the EGFR mutations

TABLE 1

Characteristics of the studied samples taken from different cell lines.

| Class | Cell Line | Histology | Mutation | Sensor Array | | GC-MS (column 1) | | GC-MS (column 2) | |
|---|---|---|---|---|---|---|---|---|---|
| EGFR | H3255 | Adeno | L858R | 4 | 10 | — | 6 | — | 9 |
| | H820 | Adeno | EX19 | 3 | | 1 | | 2 | |
| | H1650 | Adeno | EX19 | 3 | | 1 | | — | |
| | H1975 | Adeno | L858R T790M | — | | 1 | | — | |
| | HCC4006 | Adeno | EX19 | — | | 3 | | 3 | |
| | H2279 | Adeno | EX19 | — | | — | | 4 | |
| KRAS | A549 | Adeno | G12S | 3 | 14 | 2 | 6 | 1 | 5 |
| | H2009 | Adeno | G12A | 2 | | 1 | | 1 | |
| | H460 | Large Cell | Q61H | 7 | | 2 | | — | |
| | NE18 | Squamous | n/a | 2 | | 1 | | 3 | |
| ALK | H2228 | Adeno | n/a | 8 | 8 | — | — | 5 | 5 |
| WT | H322 | Adeno | | 1 | 5 | — | 5 | — | 12 |
| | H1703 | Adeno | | 2 | | — | | 1 | |
| | H125 | Adeno | | 2 | | — | | 1 | |
| | H1435 | Adeno | | — | | 3 | | — | |
| | Calu3 | Adeno | | — | | 2 | | — | |
| | HCC15 | Squamous | | — | | — | | 4 | |
| | H520 | Squamous | | — | | — | | 2 | |
| | HCC193 | Adeno | | — | | — | | 4 | |

Example 12

Headspace Analysis Using the Gold Nanoparticle (GNP) Sensor Array

The headspace samples of Example 11 were tested using a sensor array having four chemiresistor sensors of gold nanoparticles that were capped with two different organic ligands, namely decanethiol and octadecanethiol. The sensor array was prepared and fabricated as described in Peng et al. (Nature Nanotechnol (2009) 4(10) 669; Dovgolevsky et al. (Small (2008) 4(11) 2059); Dovgolevsky et al. (Small (2009) 5(10) 1158); and Peng et al. (Nano Lett (2008) 8(11) 3631), the contents of each of these references are hereby incorporated in their entirety.

Figure 15B:
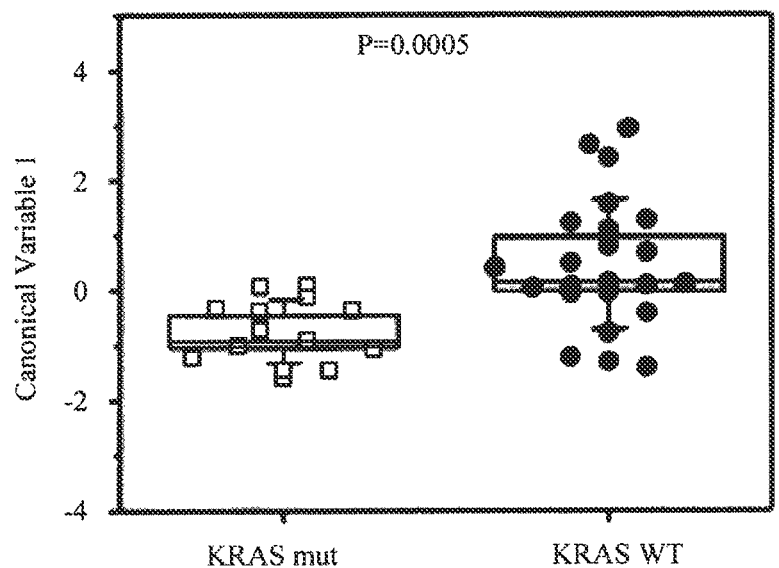
Figure 15C:
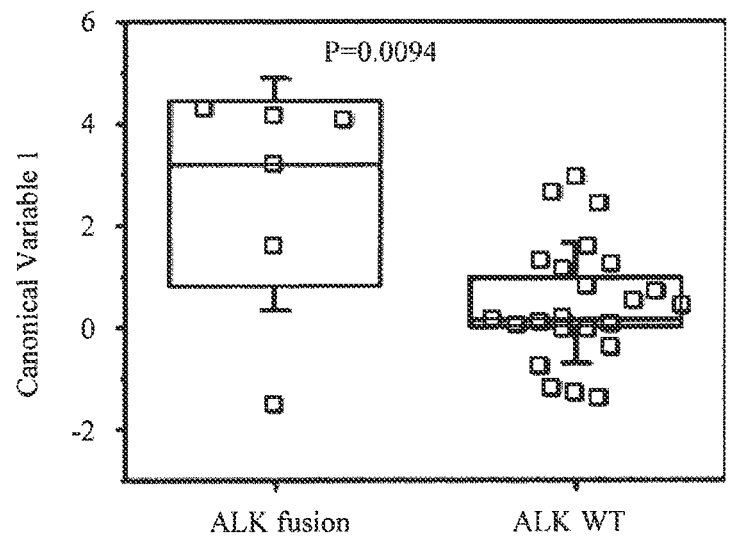
Figure 15D:
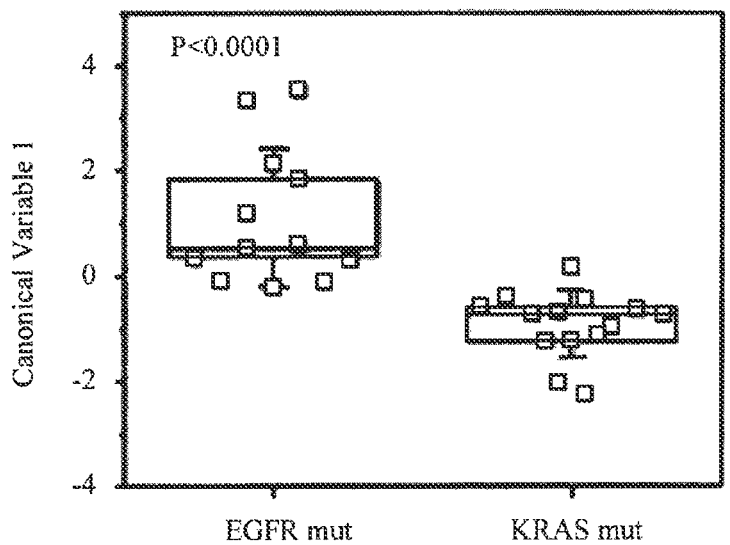
Figure 15E:
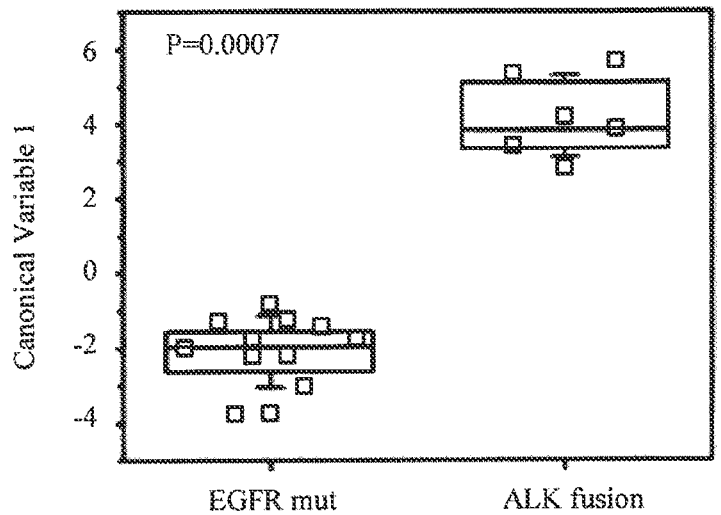
Figure 15F:
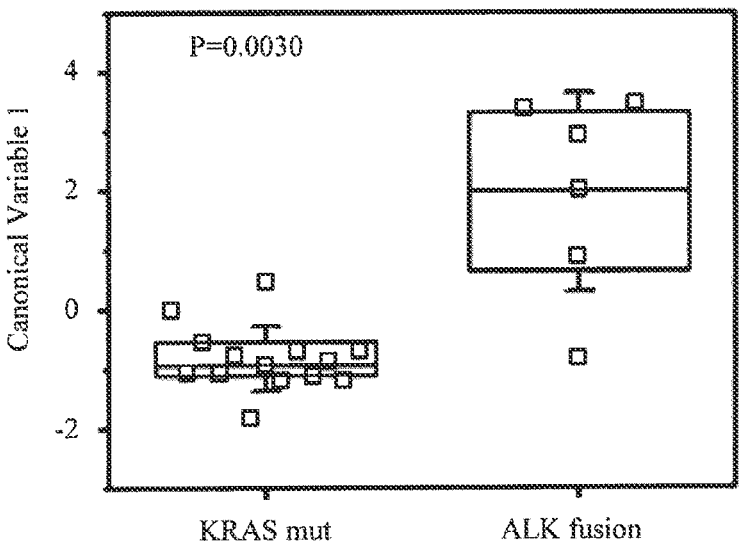
Figure 15G:
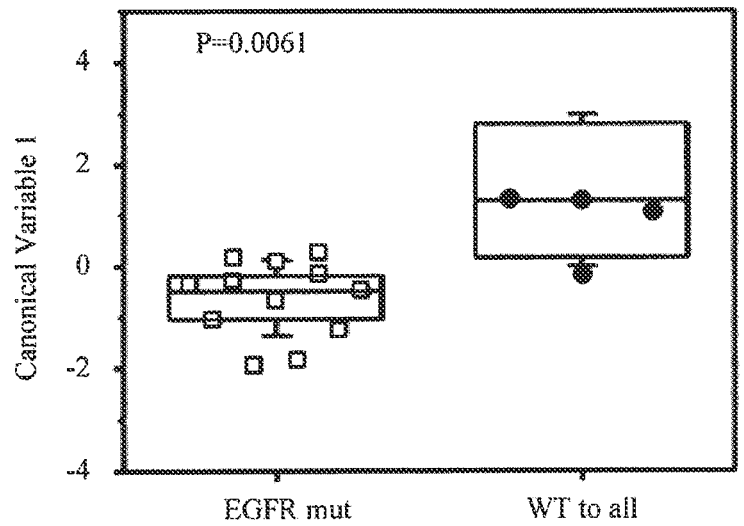
Figure 15H:
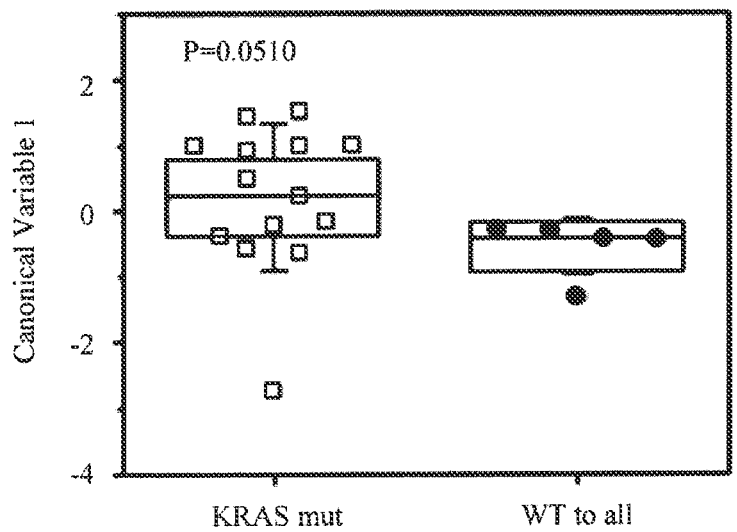
Figure 15I:
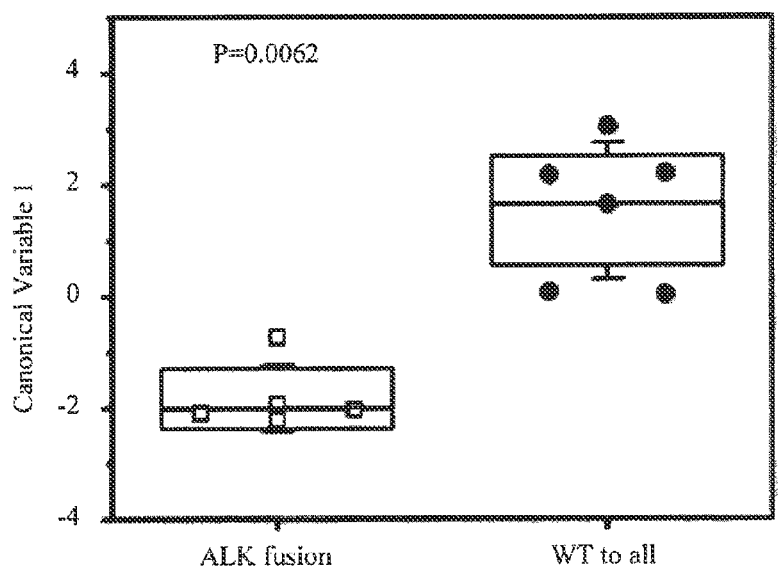

The signals obtained from the sensor array were analyzed using discriminant factor analysis (DFA; Ionescu et al., Analyst (2002) 127 1237). Four features were read out per sensor that relate to the normalized resistance change after exposure could be clearly distinguished from the EGFR WT headspace samples (samples which are characterized by KRAS mutations, ALK fusion genes and WT to all) along the DF1 axis. The DF1 values of the two study groups that were calculated from features of three sensors (Table 2) formed well-separated clusters (p<0.0001). Leave-one-out cross validation was used to estimate the classification success rate. The results in terms of correct and false classifications are represented in Table 2. The sensitivity, specificity and accuracy of the classification were determined as 70%, 100% and 92%, respectively. Clear volatile signatures were also obtained for the KRAS mutations and ALK fusion genes (FIGS. 15B and 15C). The three volatile biomarker tests shown in FIGS. 15A-15C allow classifying of any unknown headspace sample. However, due to the limitations in sensitivity and specificity of the prototype genetic volatile tests, only 65% of the test samples could be correctly identified based on their classifications during the separate leave-one-out cross validation of tests A-C. Thus, one or more test samples could be misclassified or result in an unambiguous classification.

TABLE 2

Classification success estimated through leave-one-out cross validation of the nine binary tests A-I that are shown in FIGS. 15A-15I.

| Test | Test group | Control group | TP | TN | FP | FN | Sensitivity[1] | Specificity[2] | Accuracy[3] |
|---|---|---|---|---|---|---|---|---|---|
| A | EGFR mut | KRAS mut, ALK fusion, WT to all | 7 | 27 | 0 | 3 | 70% | 100% | 92% |
| B | KRAS mut | EGFR mut, ALK fusion, WT to all | 11 | 18 | 5 | 3 | 79% | 78% | 78% |
| C | ALK fusion | EGFR mut, KRAS mut, WT to all | 5 | 29 | 0 | 3 | 63% | 100 | 92% |
| D | EGFR mut | KRAS mut | 7 | 14 | 0 | 3 | 70% | 100% | 89% |
| E | EGFR mut | ALK fusion | 10 | 6 | 2 | 0 | 100% | 75% | 89% |
| F | KRAS mut | ALK fusion | 13 | 5 | 3 | 1 | 93% | 63% | 82% |
| G | EGFR mut | WT to all | 8 | 4 | 1 | 2 | 80% | 80% | 80% |
| H | KRAS mut | WT to all | 7 | 4 | 1 | 7 | 50% | 80% | 58% |
| I | ALK fusion | WT to all | 5 | 5 | 0 | 3 | 63% | 100 | 77% |

[1]Sensitivity = TP/(TP + FN)
[2]Specificity = TN/(TN + FP)
[3]Accuracy = (TP + TN)/(TP + TN + FP + FN)

Figure 16:
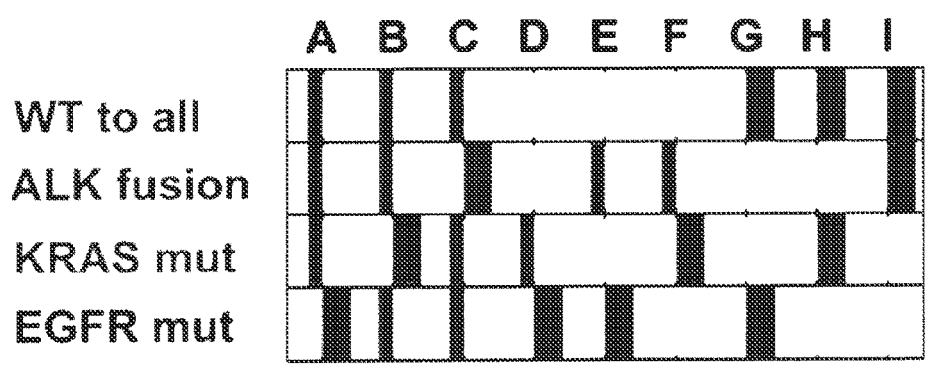
FIG. 16. The expected results of the nine tests A-I for EGFR and KRAS mutations (mut), ALK fusion and WT to all in the form of a barcode representation. Positive and negative test results are depicted by a thick bar on the right and a thin bar on the left, respectively.

The sensor system was then trained to distinguish between all four study groups by means of an additional set of six binary tests, each includes two groups (FIGS. 15D-15I). Hence, each sample was included in three of the six tests D-I, in addition to being included in all three comprehensive tests A-C. FIG. 16 shows the expected results of the nine-test-assay A-I for the four groups of genetic mutations in form of a barcode representation, whereby positive and negative test results are depicted by a thick bar on the right and a thin bar on the left, respectively. Each barcode shows six bars, corresponding to the six relevant tests from tests A-I, while the spaces of the three irrelevant tests for each sample are left clear. Due to the relatively small number of samples, some of the tests provided DF1 values which were not as well separated as compared to the DF1 values of tests A-C in which each test contained all 37 samples. For example, the identification of the KRAS mutations failed in comparison to the small and heterogeneous control group of genetic mutations that are all WT, due to one sample which provided substantially different DF1 values as compared to the other KRAS samples (FIG. 15H; Table 2). Nonetheless, test H was not excluded due to its positive predictive value of 88%.

The classification success of the volatile signature was estimated through a global leave-one-out cross validation procedure. For this purpose one sample was excluded at each time and the DF1 distribution for tests A-I was calculated using the relevant subsets of the remaining 36 samples as training sets. The left-out sample was then blinded and projected onto all nine DFA maps A-I. The classification results were represented in the form of a barcode, as described above. The barcodes of the blinded samples contained nine bars, six of which stem from the six tests that are relevant for the sample's genetic mutation and three are arbitrary results of the three irrelevant tests. The samples were identified by comparing the obtained barcodes to the expected barcodes for EGFR and KRAS mutations, ALK fusion and WT to all. Best-match classifications in the over-defined system A-I lead to the correct identification of 76% of the blinded samples, improving the classification success by 11% as compared to the classification based on tests A-C solely. The over-defined A-I system yielded classification ambiguities due to incorrect results of the separate tests of only 8% of the samples.

The present invention thus provides a volatile signature of EGFR and KRAS mutations and ALK fusion genes which allows the discrimination of cells having these mutations from cancer cells having other genetic mutations that are WT to the three mutations. The present invention further discloses a volatile signature assay based on nine binary tests that provides improved identification of samples in a simulated blind test.

Example 13

Headspace Sampling Using GC-MS

The headspace samples of Example 11 were tested for identifying the volatile biomarkers using two different GC-MS systems. System 1: CC HP 6890; MS-5973; Agilent Technologies Ltd.; H5-5MS capillary column (5% phenyl methyl siloxane; 30 m in length, 0.25 mm internal diameter, 0.25 mm in thickness, column pressure: 8.22 PSI, column flow rate: 1.0 ml per min.); splitless mode; oven profile as described in Barash et al. (Small (2009) 5(22) 2618). System 2: GCMS-QP2010, Shimadzu Corporations; capillary column SLC-5MS (30 m length, 0.25 mm i.d., 0.5 µm thickness, column pressure: 23.4 kPa, column flow rate: 0.7 mL/min.); splitless mode; oven temperature profile: 35° C., 5 min, 5° C./min to 180° C., 13.5° C./min to 290° C., 1 min. The GC-MS analysis was preceded by solid phase microextraction (SPME) for pre-concentrating the volatile biomarkers. A manual SPME holder with a divinylbenzene/carboxen/polydimethylsiloxane coated extraction fiber (Sigma-Aldrich, Israel) was inserted into the thermal desorption device for 30 min before being delivered to the CC-MS. The fiber was then inserted into the CC injector (direct mode) for thermal desorption at 270° C. The identification of the VOC biomarkers was performed by a spectral library match using the Automated Mass Spectral Deconvolution and Identification System (ADMIS) software. The data was processed using the open source XCMS package version 1.22.1 for R environment (http://metlin.scripps.edu/download/) which provides m/z and retention times. Statistical analysis was carried out using SAS JMP, Version 8.0 (SAS Institute Inc., Cary, N.C., USA, 1989-2005) for Wilcoxon/Kruskal-Wallis tests.

The chemical composition of the cell line headspace of Example 11 was analyzed in search of statistically significant differences between the volatile biomarkers of EGFR and KRAS mutations and ALK fusion genes. Multiple samples were obtained from the headspace of (i) the empty medium and (ii) the immortal bronchial epithelium cell line MINA 3KT as controls. In order to avoid systematic errors and maximize the reliability of the results, the samples were divided into two sets which were analyzed using two different GC-MS columns as detailed above. Statistically significant differences of the volatile biomarker composition in the headspace of cell lines having different genetic mutations were observed. These differences accord with the DFA volatile signatures from the signals of the sensors of organically functionalized gold nanoparticles. Elevated or reduced concentrations of some volatile biomarkers were observed for the studied genetic mutations, as compared to the empty medium. Without being bound by any theory or mechanism of action, this could indicate consumption or production of these substances through the mutated NSCLC cells. Table 3 lists the volatile biomarkers exhibiting the same trends for both GC-MS columns that were statistically significant for one or both columns. The triethylamine concentration showed a decrease in the headspace of NSCLC cells having all of the studied mutations, except for KRAS. The aromatic compounds, toluene and styrene, were found in increased concentrations in the headspace of NSCLC cells having all of the studied mutations, except for KRAS. An observed decrease in the concentration of aldehydes in the headspace of most NSCLC cell lines as compared to the control medium was observed. In comparison, no significant change in the aldehyde concentration was observed in the headspace of the immortal control cells as compared to the medium. Two alcohols were found in increased concentrations in the headspace of the EGFR mutated cell lines.

TABLE 3

Summary of the statistically significant changes in the headspace of cancer cells with different genetic mutations as compared to the empty medium. Increase or decrease in the concentrations of VOCs that occur in > 80% of the studied samples as compared to the control are indicated.

| Compound | Structure | Statistically Significant Trends[1] | |
|---|---|---|---|
| | | GC-MS (Column 1) | GC-MS (Column 2) |
| Amine | | | |
| Triethylamine | 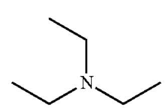 | EGFR↓ ALK↓ WT↓ | EGFR↓ WT↓ |
| Aromatic Compounds | | | |
| Toluene | 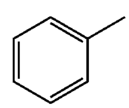 | EGFR↑* ALK↑ WT↑ | EGFR↑ WT↑* |
| Styrene | 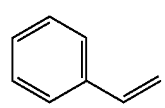 | EGFR↑ | EGFR↑* |
| Aldehydes | | | |
| Benzaldehyde | 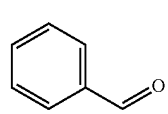 | KRAS↓ | KRAS↓* |
| Benzaldehyde, 2-hydroxy | 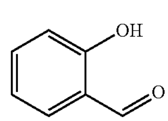 | KRAS↓ ALK↓ | KRAS↓ |
| Decanal | 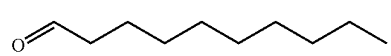 | EGFR↓ ALK↓ | EGFR↓* |

TABLE 3-continued

Summary of the statistically significant changes in the headspace of cancer cells with different genetic mutations as compared to the empty medium. Increase or decrease in the concentrations of VOCs that occur in > 80% of the studied samples as compared to the control are indicated.

| Compound | Structure | Statistically Significant Trends[1] | |
|---|---|---|---|
| | | GC-MS (Column 1) | GC-MS (Column 2) |
| Alcohols | | | |
| Phenol | [structure] | EGFR↑* | EGFR↑ |
| 2-Ethyl-1-hexanol | [structure] | EGFR↑* | EGFR↑ |

↑: Volatile biomarkers increased in NSCLC cells compared to medium
↓: Volatile biomarkers decreased in NSCLC cells compared to medium
*: sub-significant changes The present invention thus provides the identification or exclusion of KRAS mutations and ALK fusion genes in the same diagnostic test through headspace sampling of lung cells. This could be used in operating rooms as a fast and cost-effective method to identify patients who would most likely benefit from EGFR tyrosine kinase inhibitors therapy. The simultaneous identification or exclusion of KRAS mutations and ALK fusion genes in the same diagnostic test could indicate when chemotherapy should be favored over EGFR tyrosine kinase inhibitors treatment, and when the surgery of stage IA and IB lung cancer patients should be followed without delay by adjuvant chemotherapy. The present invention further provides breath analysis for the identification of genetic volatile signature which is associated with lung cancer.

Example 14

Classification of Lung Cancer Histologies

In order to classify the histologies of lung cancer cells, 20 NSCLC cell lines, sub-categorized to 14 adenocarcinoma cell lines and 6 squamous cell carcinoma, and 4 SCLC cell lines (Table 4) were obtained from the Colorado cell bank registry and were grown in 100 mm cell-culture dishes from seeding (~$2\times10^6$ cells) up to 95% confluency ($7\times10^6$ cells), using a two dimensional medium (designated "medium 1") under standard conditions (RPMI 1640 medium+10% FBS; 5% $CO_2$ environment). 7 immortal bronchial epithelium (IBE) cell lines (Table 4) were grown likewise in 100 mm cell-culture dishes from seeding (~$2\times10^6$ cells) up to 95% confluency ($7\times10^6$ cells), using another two dimensional medium (designated "medium 2") under standard conditions (BEBM 1640 medium+10% FBS; 5% $CO_2$ environment). Medium 1 (in 7 replicas) and medium 2 (in 5 replicas) served as a baseline (background) control for the lung cancer cell lines and IBE cell lines, respectively (same incubation time and conditions, but without the cells). Each cell culture was placed in a 150 mm dish. Two Ultra II SKC™ badges with Tenax TA as a sorbent (265 mg; SKC Inc.) were placed above the dish for absorbing the headspace atmosphere during the total growth time (median time 68 hours; range 60-72 hours).

TABLE 4

Characteristics of the headspace of lung cancer cell lines. Headspace samples were collected in duplicates (except for NE18 measured by the GNP sensors)

| | Histology | | Cell Line | Growth Medium | GNP sensors | | GC-MS | |
|---|---|---|---|---|---|---|---|---|
| Lung Cancer | NSCLC | Adeno-carcinoma | H1650 | Medium 1 | 1 | 14 | 1 | 14 |
| | | | H820 | | 1 | | 1 | |
| | | | A549 | | 1 | | 1 | |
| | | | H1975 | | 1 | | 1 | |
| | | | H4006 | | 3* | | 3* | |
| | | | H1435 | | 3* | | 3* | |
| | | | Calu-3 | | 1 | | 1 | |
| | | | A549 | | 1 | | 1 | |
| | | | H2009 | | 1 | | 1 | |
| | | | Calu-3 | | 1 | | 1 | |
| | | Squamous cell carcinoma | HCC95 | | 2* | 5 | 2* | 6 |
| | | | HCC15 | | 2* | | 2* | |
| | | | H226 | | 1 | | 1 | |
| | | | NE18 | | 0 | | 1 | |

TABLE 4-continued

Characteristics of the headspace of lung cancer cell lines. Headspace samples were collected in duplicates (except for NE18 measured by the GNP sensors)

| Histology | Cell Line | Growth Medium | GNP sensors | | GC-MS | |
|---|---|---|---|---|---|---|
| SCLC | H774 | | 1 | 4 | 1 | 4 |
| | H69 | | 1 | | 1 | |
| | H187 | | 1 | | 1 | |
| | H526 | | 1 | | 1 | |
| Immortal bronchial epithelium | Minna 3KT | Medium 2 | 7* | 7 | 7* | 7 |

*Samples from cell line replicas.

The headspace VOCs were identified using GC-MS as described in Example 13 (system 1). The GC-MS analysis was preceded by solid phase microextraction (SPME) for pre-concentrating the headspace VOCs. After the headspace collection process, the Tenax sorbent material from one collection badge per cell line was transferred to a 350 ml thermal desorption chamber made of stainless steel that was pre-heated to 270° C. After 10 min, a manual SPME holder with a divinylbenzene/carboxen/polydimethyl siloxane coated extraction fiber (Sigma-Aldrich, Israel) was inserted into the thermal desorption device for 30 min before being delivered to the GC-MS. The fiber was then inserted into the GC injector (direct mode) for thermal desorption at 270° C. The identification of the VOCs was performed as described in Example 13.

The Tenax sorbent material from the second collection badge per cell line was transferred to a 750 ml stainless steel thermal desorption chamber that was pre-heated to 270° C. and kept at said temperature for 10 min. The obtained headspace samples were analyzed using cross-reactive chemiresistors that were based on spherical gold nanoparticles (GNPs, core diameter: 3-4 nm) coated with different organic functionalities (decanethiol, hexanethiol, butanethiol and 2-mercaptobenzoxazole). The organically functionalized GNPs were synthesized as described in Dovgolevsky et al. (Small (2008) 4(11) 2059-2066); Dovgolevsky et al. (Small (2009) 5(10) 1158-1161); and Dovgolevsky et al. (J Phys Chem C (2010) 114(33) 14042-14049); and dispersed in chloroform. Chemiresistive layers were formed by drop-casting the solution onto semi-circular microelectronic transducers, until a resistance of several $M\Omega$ was reached. The device was dried for 2 h at ambient temperature and then baked overnight at 50° C. in a vacuum oven. The microelectronic transducers consisted of ten pairs of circular interdigitated gold electrodes that were deposited by an electron-beam evaporator TFDS-870 (Vacuum Systems & Technologies, Petah-Tikva, Israel) on a piece of device quality silicon wafer capped with 300 nm thermal oxide (Silicon Quest International, Nevada, US). The outer diameter of the circular electrode area was 3 mm, and the gap between two adjacent electrodes and the width of each electrode were both 20 µm.

Lung cancer-histology specific patterns were determined from the collective response of the GNP sensors by applying support vector machine (SVM) analysis as statistical pattern recognition algorithm. Cross-validation was utilized to evaluate the classification success in terms of specificity, sensitivity and accuracy by randomly dividing each sub-population into two sets, which were then used as a training set and a test set. Cross validation has a training stage, followed by a test stage. A new test set that is blinded against the model is created each time prior to the training stage. The model is build based on the remaining samples, i.e. the training set. Thus, the method is less biased towards any group that is initially selected as a test set. Cross-validation attempts to remove the bias by generating all possible test sets, giving a stronger statistical impact to the choice of fixed training and test sets thus making it superior in the case of a relatively limited sample size. All possible combinations of division into test- and training sets were tested and the results were averaged. The results were stable against changing the number of folds in the cross-validation.

In order to discriminate between lung cancer and healthy states, chemical analysis of the substances in the cell line headspace was performed. GC-MS/SPME analysis identified over 1000 different VOCs in each headspace sample. First, VOCs that were present in >80% of the cell lines were identified as those which are released or produced by the cells. Second, changes in the VOCs' concentrations in >80% of the lung cells and in <20% of the respective control medium were used to determine the production or consumption of VOCs from the medium. The results are summarized in Table 5. The VOCs that characterize lung cancer states and sub-histologies thereof include aldehydes, alkanes, ketones, alcohols and benzene derivatives. Table 5 shows marked differences in the headspace composition of the lung cancer cell lines and their simulated healthy controls, i.e. the replicas of the IBE cell line. The IBE cell line with no other cancer specific modifications was used as a model for the healthy lung cells. The headspace of the IBE cell line was almost identical to the headspace of control medium 2, with only slightly elevated levels of 1,3-dimethyl-benzene. In contrast, the lung cancer cells significantly alter the headspace atmosphere. The direct comparison between lung cancer and IBE states requires a correction of the VOC concentrations due to the differences in their growth medium (medium 1 and 2). The IBE cell line requires a growth medium containing more nutrients in order to achieve sufficient cell growth. Thus, the average VOC concentrations in the headspace of medium 1 and 2 were subtracted from the headspace concentrations of the lung cancer and IBE cell lines, respectively. Only the aldehyde decanal showed a significant difference between the lung cancer and the IBE states (Table 5). SVM analysis and cross validation showed that the decanal concentration in the headspace of the lung cancer cells strongly decreases as compared to the IBE control cells allowing a complete discrimination between lung cancer and IBE states with 100% accuracy (Table 6(a)).

TABLE 5

Trends of VOC concentrations of the headspace samples that characterize lung cancer (LC) and sub-histologies thereof

| Group | Compound | Medium 1 → LC | Medium 2 → IBE | IBE# → LC# | Medium 1 → NSCLC | Medium 1 → SCLC | SCLC → NSCLC | Medium 1 → Adenocarcinoma | Medium 1 → Squamous cell carcinoma | Squamous cell carcinoma → Adenocarcinoma |
|---|---|---|---|---|---|---|---|---|---|---|
| Aldehydes | Benzaldehyde | | | | | | ↓** | | ↓** | ↑* |
| | Nonanal | | | | | ↓** | ↑** | | ↓** | ↑** |
| | Decanal | ↓* | | ↓*** | ↓** | ↑** | ↓** | ↓** | ↓** | |
| Alkanes | Tetradecane | | | | | ↓** | ↑** | | | |
| | 5-methyl-Tridecane | | | | | ↓** | ↑** | | ↓** | ↑** |
| Ketones | 6-Methy-5-Heptene-2-One | ↑* | | | ↑* | ↓** | ↑** | ↑* | | ↑* |
| | Acetophenone | | | | | ↑** | ↓** | | | ↑* |
| Alcohols | 2,4-bis(1,1-Dimethyl-ethyl)Phenol | ↑** | | | ↑** | | ↓* | ↑* | ↑* | |
| | 2-Ethyl-1-Hexanol | | | | ↑* | ↓** | ↑** | ↑* | ↓* | ↑** |
| Benzene derivatives | 1,3-bis(1,1-Dimethylethyl)-Benzene | ↑* | | | ↑* | ↓** | ↑** | ↑** | | ↑** |
| | 1,3-Dimethyl-Benzene | | ↑* | | | ↓** | ↑** | ↑** | ↓** | ↑*** |
| | Styrene | ↓* | | | ↑* | ↑* | ↓* | ↑* | | ↑** |

VOCs' abundance was corrected by subtracting the mean value of corresponding medium.
↑ Increase in concentration
↓ Decrease in concentration
*$p < 0.05$
**$p < 0.01$
***$p < 0.0001$ 12 compounds that showed significant differences in their concentration between SCLC and NSCLC were then identified. SVM analysis further identified three substances (decanal, acetophenone and 1,3-bis(1,1-dimethylethyl)-benzene) as main contributors to the discrimination between the two groups, which allowed distinction of NSCLC from SCLC with a sensitivity of 100% and a specificity of 75% (Table 6(b)).

Adenocarcinoma and squamous cell carcinoma are sub-histologies of NSCLC. 7 compounds that include aldehydes, 1 alkane, 2 ketones, 1 alcohol and 3 benzene derivatives were identified. Using SVM analysis, 2-ethyl-1-hexanol, 1,3-dimethyl-benzene and 1,3-bis(1,1-dimethylethyl)-benzene were determined as compounds which afford the best discrimination between these sub-histologies. These compounds were found at higher concentrations in the headspace of adenocarcinoma as compared to the headspace of squamous cell carcinoma. Using these three compounds, adenocarcinoma could be distinguished from squamous cell carcinoma with a sensitivity, specificity and accuracy of 100%, 67% and 90%, respectively (Table 6(c)).

TABLE 6

Classification success of the GC-MS chemical analysis: Number of correct and incorrect sample classifications estimated by supportive vector machine (SVM) and cross validation (6a) Lung Cancer (LC) and the Immortal Bronchial Epithelium (IBE) cell lines, using only the abundance of decanal

| | Classified as LC | Classified as IBE |
|---|---|---|
| LC* | 24 | 0 |
| IBE* | 0 | 7 |

(6b) Non Small Cell Lung Cancer (NSCLC) and Small Cell Lung Cancer (SCLC) cell lines, using the abundance of decanal, 1,3-bis(1,1-dimethylethyl)-benzene, and acetophenone

| | Classified as NSCLC | Classified as SCLC |
|---|---|---|
| NSCLC | 20 | 0 |
| SCLC | 1 | 3 |

TABLE 6-continued

Classification success of the GC-MS chemical analysis: Number of correct and incorrect sample classifications estimated by supportive vector machine (SVM) and cross validation (6c) Adenocarcinoma and the squamous cell carcinoma cell lines, using the abundance of 1,3-dimethyl-benzene, 1,3-bis(1,1-dimethylethyl)-benzene, and 2-ethyl-1-hexanol

| | Classified as adenocarcinoma | Classified as squamous cell carcinoma |
|---|---|---|
| Adenocarcinoma | 14 | 0 |
| Squamous cell carcinoma | 2 | 4 |

*The abundance of decanal in the different media in which cells were grown was corrected by subtracting the mean value in each corresponding medium Lung cancer specific patterns were obtained from the collective responses of 1 to 3 GNP sensors coated with different organic functionalities. SVM analysis was used to select the sensors based on their discriminative abilities, from a reservoir of 18 available organically functionalized GNP chemiresistors that were exposed simultaneously to the headspace samples. Each sensor underwent a rapid and fully reversible change in electrical resistance upon exposed to the sample. Several sensing features were deduced from the time-dependent responses that related to the net resistance change upon exposure, DR, at the start, mid-range or end of the exposure, to the resistance response normalized with respect to the baseline resistance, $DR/R_0$, or to the area under the response curve, A. Each of the 18 GNP sensors of the reservoir responded to all (or to a certain subset) of the VOCs found in the samples. Lung cancer-specific patterns were obtained from the collective response of the GNP sensors by applying SVM analysis as a statistical pattern recognition algorithm.

Figure 17A:
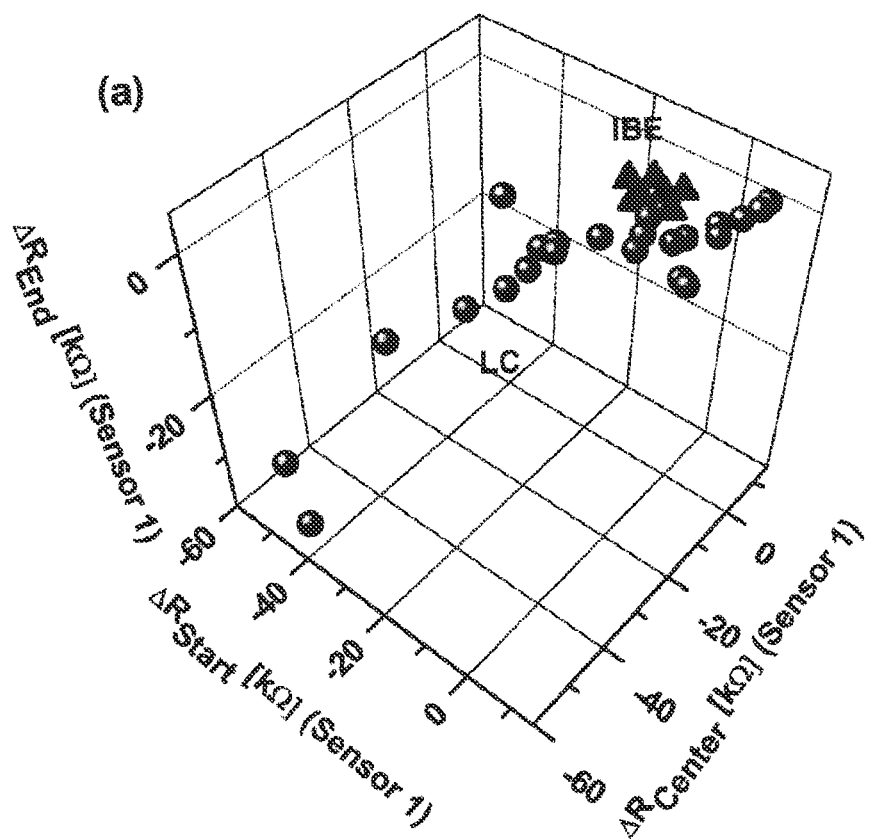

Three sensing features from a single sensor (coated with decanethiol; $DR_{Start}$, $DR_{Mid\text{-}range}$, and $DR_{end}$) were selected through SVM for the distinction between the lung cancer states and the IBE controls. The number of input parameters was kept low enough to avoid over-fitting during the SVM analysis. The pseudo-three dimensional representation of the three sensing features in FIG. 17A shows that the two states can clearly be distinguished. The sensitivity, specificity and accuracy of the identification of lung cancer from headspace samples were determined as 96%, 86% and 93%, respectively.

Figure 17B:
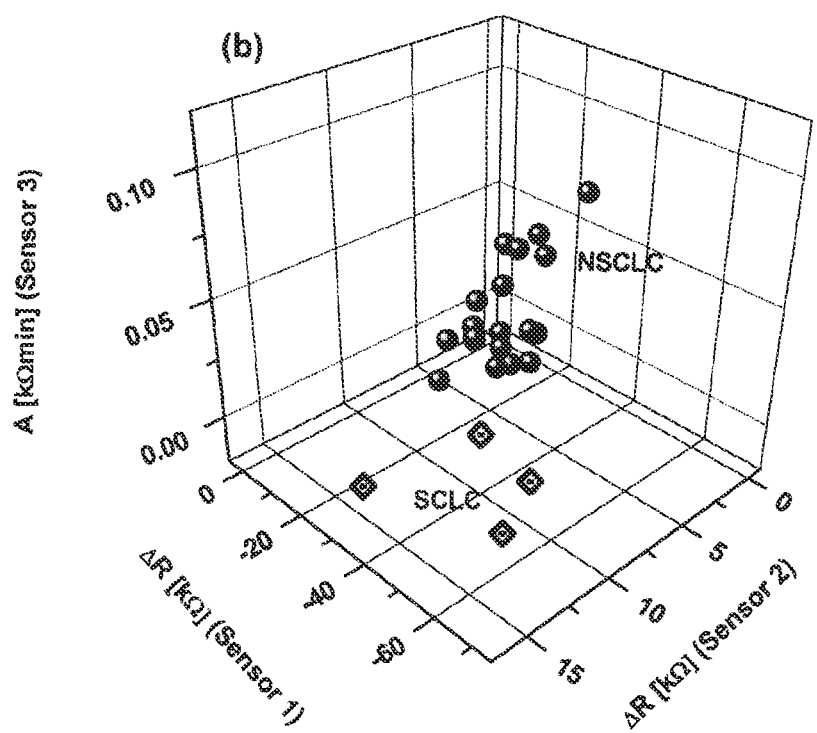

FIG. 17B shows that NSCLC can be well distinguished from SCLC using one feature from each of the three sensors (GNP coated with decanethiol, hexanethiol and butanethiol). No correction of the sensing features was necessary in this case since all lung cancer cell lines were grown in medium 1. SVM and cross validation yielded a sensitivity of 100%, reasonable specificity (75%) and high accuracy (96%) for the NSCLC distinction.

Figure 17C:
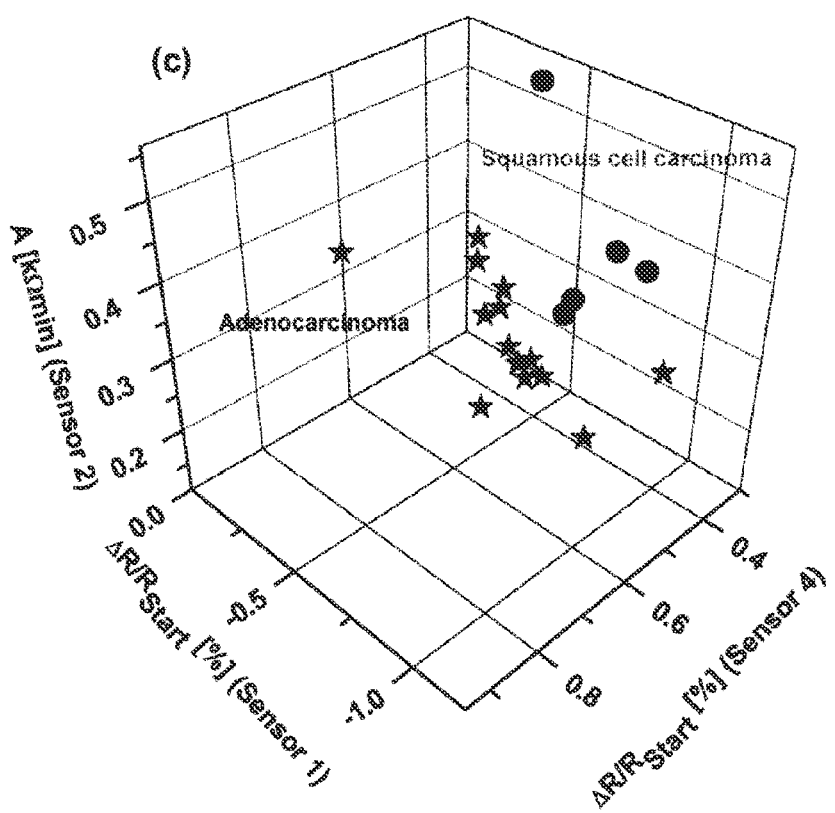

FIG. 17C shows the distinction between the headspace of the NSCLC sub-histologies, adenocarcinoma and squamous cell carcinoma, using three features from three sensors (GNP coated with decanethiol, hexanethiol and 2-mercaptobenzoxazole). High values for the sensitivity (86%), specificity (100%) and accuracy (90%) were obtained through SVM and cross validation.

It is appreciated by persons skilled in the art that the present invention is not limited by what has been particularly shown and described hereinabove. Rather the scope of the present invention includes both combinations and sub-combinations of various features described hereinabove as well as variations and modifications. Therefore, the invention is not to be constructed as restricted to the particularly described embodiments, and the scope and concept of the invention will be more readily understood by references to the claims, which follow.

The invention claimed is:

1. A method of differentiating between a test subject having lung cancer associated with a mutation in Epidermal Growth Factor Receptor (EGFR) and subjects having lung cancer associated with a genetic alteration selected from a mutation in KRAS, an ALK-ELM4 translocation and CMET amplification, the method comprising the steps of:
   a) obtaining a breath sample from the test subject;
   b) determining a level of at least one volatile organic compound associated with lung cancer in the breath sample; and
   c) comparing the level of the at least one volatile organic compound from the breath sample with the level of said at least one volatile organic compound in a negative control sample of cells not having a mutation in EGFR, whereby a significantly different level of said at least one volatile organic compound in the breath sample as compared to the level of said compound in the negative control sample is indicative of the presence of mutation in EGFR.

2. The method according to claim 1, wherein the at least one volatile organic compound associated with lung cancer is selected from the group consisting of 4-methyl-1-heptanol, acetic acid octyl ester, decane, 3-methyl-decane, octanal, pentadecanenitrile, and tetradecene; or selected from the group consisting of 4-methyl-1-heptanol, 6-methyl-1-heptanol, 2-ethyl-1-hexanol, acetic acid octyl ester, benzaldehyde, decane, 3-methyl-dodecane, tetrahydrofuran, isopropyl myristate, octanal, pentadecanenitrile, 2,2,4-trimethyl-pentanenitrile, 2,2,4-trimethyl-3-carboxyisopropyl-isobutyl ester pentanoic acid, phenol, styrene, tetradecane, 4-methyl-tetradecane, toluene, tridecane, 6-methyl-tridecane, and undecane; or selected from the group consisting of triethylamine, 2-hydroxy benzaldehyde, and decanal; or selected from the group consisting of triethylamine, toluene, styrene, benzaldehyde, 2-hydroxy benzaldehyde, decanal, phenol and 2-ethyl-1-hexanol.

3. The method according to claim 1, wherein the step of determining the level of at least one volatile organic compound in the breath sample comprises the use of at least one technique selected from the group consisting of an olfactory system, Gas-Chromatography (GC), GC-lined Mass-Spectrometry (GC-MS), Proton Transfer Reaction Mass-Spectrometry (PTR-MS), and Quartz Crystal Microbalance (QCM).

4. The method according to claim 1, wherein the level of the at least one volatile organic compound in the breath sample is increased as compared with the level of said compound in the control sample; or wherein the level of the at least one volatile organic compound in the breath sample is decreased as compared with the level of said compound in the control sample.

5. The method according to claim 1, wherein the at least one volatile organic compound in the breath sample is a plurality of volatile organic compounds, and wherein a combination of levels of each of the plurality of volatile organic compounds in the breath sample a pattern which is significantly different from a pattern of the combination of levels of each of the plurality of volatile organic compounds in the negative control sample.

6. The method according to claim 5, wherein the pattern is analyzed with a pattern recognition analyzer.

7. The method according to claim 6, wherein the pattern recognition analyzer comprises at least one algorithm selected from the group consisting of principal component analysis (PCA), artificial neural network algorithms, multilayer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART), partial least squares (PLS), multiple linear regression (MLR), principal component regression (PCR), discriminant function analysis (DFA), linear discriminant analysis (LDA), cluster analysis, and nearest neighbor.

8. The method according to claim 1, wherein the test subject is a mammal.

9. The method according to claim 1, wherein the at least one volatile organic compound associated with lung cancer is selected from the group consisting of triethylamine, toluene, styrene, decanal, phenol and 2-ethyl-1-hexanol.

10. The method according to claim 1, wherein the test subject is human.

11. The method according to claim 1, wherein the mutation in EGFR is a T790M EGFR mutation.

12. A method for treating lung cancer, comprising:
   (i) determining that a patient has a lung cancer associated with a mutation in Epidermal Growth Factor Receptor (EGFR), as differentiated from patients having lung cancer associated with a genetic alteration selected from a mutation in KRAS, an ALK-ELM4 translocation and CMET amplification, by a method comprising the steps of:
   a) obtaining a breath sample from the patient;
   b) determining a level of at least one volatile organic compound associated with lung cancer in the breath sample; and
   c) comparing the level of the at least one volatile organic compound from the breath sample with the level of said at least one volatile organic compound in a negative control sample of cells not having a mutation in EGFR, whereby a significantly different level of said at least one volatile organic compound in the breath sample as compared to the level of said compound in the negative control sample is indicative of the presence of mutation in EGFR in the patient, and (ii) administering a tyrosine kinase modulator to the patient having a lung cancer associated with the mutation in EGFR.

13. The method according to claim 12, wherein the tyrosine kinase modulator is selected from the group consisting of Axitinib, Bosutinib, Cediranib, Crizotinib, Dasatinib, Erlotinib, Gefitinib, Imatinib, Lapatinib, Lestaurtinib, Nilotinib, Semaxanib, Sunitinib, and Vandetanib.

14. The method according to claim 12, wherein the at least one volatile organic compound associated with lung cancer is selected from the group consisting of 4-methyl-1-heptanol, acetic acid octyl ester, decane, 3-methyl-decane, octanal, pentadecanenitrile, and tetradecene; or selected from the group consisting of 4-methyl-1-heptanol, 6-methyl-1-heptanol, 2-ethyl-1-hexanol, acetic acid octyl ester, benzaldehyde, decane, 3-methyl-dodecane, tetrahydrofuran, isopropyl myristate, octanal, pentadecanenitrile, 2,2,4-trimethyl-pentanenitrile, 2,2,4-trimethyl-3-carboxyisopropyl-isobutyl ester pentanoic acid, phenol, styrene, tetradecane, 4-methyl-tetradecane, toluene, tridecane, 6-methyl-tridecane, and undecane; or selected from the group consisting of triethylamine, 2-hydroxy benzaldehyde, and decanal; or selected from the group consisting of triethylamine, toluene, styrene, benzaldehyde, 2-hydroxy benzaldehyde, decanal, phenol and 2-ethyl-1-hexanol.

15. The method according to claim 12, wherein the at least one volatile organic compound associated with lung cancer is selected from the group consisting of triethylamine, toluene, styrene, decanal, phenol and 2-ethyl-1-hexanol.

16. The method according to claim 12, wherein the step of determining the level of at least one volatile organic compound in the breath sample comprises the use of at least one technique selected from the group consisting of an olfactory system, Gas-Chromatography (GC), GC-lined Mass-Spectrometry (GC-MS), Proton Transfer Reaction Mass-Spectrometry (PTR-MS), and Quartz Crystal Microbalance (QCM).

17. The method according to claim 12, wherein the level of the at least one volatile organic compound in the breath sample is increased as compared with the level of said compound in the control sample; or wherein the level of the at least one volatile organic compound in the breath sample is decreased as compared with the level of said compound in the control sample.

18. The method according to claim 12, wherein the at least one volatile organic compound in the breath sample is a plurality of volatile organic compounds, and wherein a combination of levels of each of the plurality of volatile organic compounds in the breath sample forms a pattern which is significantly different from a pattern of the combination of levels of each of the plurality of volatile organic compounds in the negative control sample.

19. The method according to claim 18, wherein the pattern is analyzed with a pattern recognition analyzer.

20. The method according to claim 19, wherein the pattern recognition analyzer comprises at least one algorithm selected from the group consisting of principal component analysis (PCA), artificial neural network algorithms, multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART), partial least squares (PLS), multiple linear regression (MLR), principal component regression (PCR), discriminant function analysis (DFA), linear discriminant analysis (LDA), cluster analysis, and nearest neighbor.

* * * * *